(12) United States Patent
Komori et al.

(10) Patent No.: US 7,993,760 B2
(45) Date of Patent: *Aug. 9, 2011

(54) COMPOUND FOR USE IN ORGANIC ELECTROLUMINESCENT DEVICE AND ORGANIC ELECTROLUMINESCENT DEVICE

(75) Inventors: Masaki Komori, Fukuoka (JP); Toshihiro Yamamoto, Fukuoka (JP); Takahiro Kai, Fukuoka (JP); Masanori Hotta, Fukuoka (JP);

(73) Assignee: Nippon Steel Chemical Co., Ltd., Tokyo (JP)

( * ) Notice: Subject to any disclaimer, the term of this patent is extended or adjusted under 35 U.S.C. 154(b) by 357 days.

This patent is subject to a terminal disclaimer.

(21) Appl. No.: 12/085,447

(22) PCT Filed: Nov. 22, 2006

(86) PCT No.: PCT/JP2006/323290
§ 371 (c)(1),
(2), (4) Date: Aug. 1, 2008

(87) PCT Pub. No.: WO2007/063754
PCT Pub. Date: Jun. 7, 2007

(65) Prior Publication Data
US 2009/0302742 A1    Dec. 10, 2009

(30) Foreign Application Priority Data

Dec. 1, 2005 (JP) .................................. 2005-347990
Oct. 12, 2006 (JP) .................................. 2006-278619
Oct. 24, 2006 (JP) .................................. 2006-288568

(51) Int. Cl.
*H01J 1/63* (2006.01)
*C07D 487/04* (2006.01)
*C09K 11/06* (2006.01)

(52) U.S. Cl. ......... 428/690; 428/917; 313/504; 548/418
(58) Field of Classification Search .................. None
See application file for complete search history.

(56) References Cited

U.S. PATENT DOCUMENTS

| | | | |
|---|---|---|---|
| 5,942,340 A | 8/1999 | Hu et al. | |
| 5,952,115 A | 9/1999 | Hu et al. | |
| 6,670,054 B1 * | 12/2003 | Popovic et al. | 428/690 |
| 7,172,823 B2 | 2/2007 | Sohn et al. | |
| 7,291,406 B2 | 11/2007 | Thompson et al. | |
| 2001/0052751 A1 * | 12/2001 | Wakimoto et al. | 313/504 |
| 2002/0135296 A1 * | 9/2002 | Aziz et al. | 313/504 |
| 2003/0205696 A1 * | 11/2003 | Thoms et al. | 252/301.16 |
| 2004/0137271 A1 | 7/2004 | Sohn et al. | |
| 2007/0057250 A1 | 3/2007 | Takiguchi et al. | |

FOREIGN PATENT DOCUMENTS

| | | |
|---|---|---|
| EP | 1 956 022 A1 | 8/2008 |
| EP | 1 956 666 A1 | 8/2008 |
| EP | 2 080 762 A1 | 7/2009 |
| JP | 11-144866 A | 5/1999 |
| JP | 11-162650 A | 6/1999 |
| JP | 11-176578 A | 7/1999 |
| JP | 2002-305083 A | 10/2002 |
| JP | 2002-352957 A | 12/2002 |
| JP | 2003-515897 A | 5/2003 |
| JP | 2004-204234 A | 7/2004 |
| JP | 2005-174917 A | 6/2005 |
| JP | 2005-213188 A | 8/2005 |
| JP | 2006-13469 A | 1/2006 |
| WO | WO 2006/033538 A1 | 3/2006 |
| WO | WO 2007/063754 A1 | 6/2007 |
| WO | WO 2007/063796 A1 | 6/2007 |
| WO | WO 2008/056746 A1 | 5/2008 |

OTHER PUBLICATIONS

PCT/JP2006/323290—English translation of International Preliminary Report on Patentability and Written Opinion of the International Searching Authority (Forms PCT/IB/373; PCT/IB/338, PCT/IB/326, and PCT/ISA/237) dated Jun. 12, 2008.
PCT/JP2008/059523—International Search Report dated Aug. 12, 2008.

* cited by examiner

*Primary Examiner* — Dawn L. Garrett
*Assistant Examiner* — Andrew K Bohaty
(74) *Attorney, Agent, or Firm* — Birch, Stewart, Kolasch & Birch, LLP

(57) ABSTRACT

Disclosed are an organic electroluminescent device (organic EL device) which is improved in luminous efficiency, fully secured of driving stability, and simple in constitution and a compound for use therein. The organic electroluminescent device comprises a light-emitting layer disposed between an anode and a cathode piled one upon another on a substrate and the light-emitting layer contains a phosphorescent dopant and a compound for use in an organic electroluminescent device having two or more indolocarbazole skeletons as a host material. An example of the compound having indolocarbazole skeletons for use in the device is expressed by the following formula.

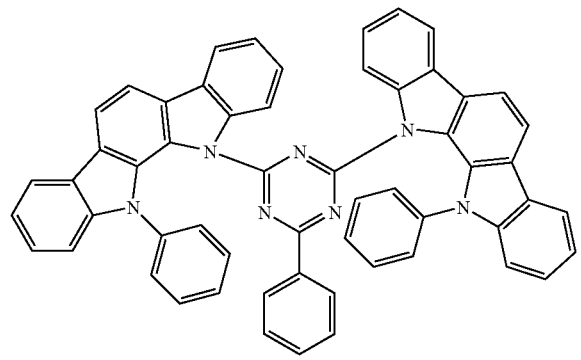

12 Claims, 1 Drawing Sheet

COMPOUND FOR USE IN ORGANIC ELECTROLUMINESCENT DEVICE AND ORGANIC ELECTROLUMINESCENT DEVICE

TECHNICAL FIELD

This invention relates to a novel compound for use in an organic electroluminescent device and to an organic electroluminescent device (hereinafter referred to as an organic EL device) and, more particularly, to an organic EL device which emits light of high luminance by simultaneous use of a phosphorescent dopant and a host compound of specific structure.

BACKGROUND TECHNOLOGY

An organic EL device of the simplest structure is generally constituted of a light-emitting layer sandwiched between a pair of counter electrodes and utilizes the following light-emitting phenomenon. Upon application of voltage to the electrodes, electrons are injected from a cathode and holes are injected from an anode and they recombine in the light-emitting layer; after recombination, the energy level in the conduction band goes back to the energy level in the valence band with release of energy in the form of light.

In recent years, organic thin films have been used in the development of EL devices. In particular, devices that comprise a hole-transporting layer of an aromatic amine and a light-emitting layer of 8-hydroxyquinoline aluminum complex (hereinafter referred to as Alq3) disposed in thin film between the electrodes have been developed following the optimization of the kind of electrodes for the purpose of improving the efficiency of carrier injection from the electrodes and enhancing the luminous efficiency. The devices of this kind have produced remarkable improvement in luminous efficiency over the conventional devices utilizing single crystals of anthracene and the like and the developmental works of organic EL devices thereafter have aimed at commercial application to high-performance flat panels featuring self luminescence and high-speed response.

The utilization of phosphorescence in place of fluorescence is experimented to enhance the luminous efficiency of the device. The aforementioned devices comprising a hole-transporting layer of an aromatic diamine and a light-emitting layer of Alq3 and many others utilize fluorescence. Now, the utilization of phosphorescence, that is, emission of light from the triplet excited state, is expected to enhance the luminous efficiency approximately three times that of the conventional devices utilizing fluorescence (singlet). To achieve this object, studies were conducted on the use of coumarin derivatives and benzophenone derivatives in the light-emitting layer, but the result was nothing but extremely low luminance. Thereafter, europium complexes were tried in the utilization of the triplet excited state, but they failed to emit light at high efficiency. A large number of inventions have been made relating to phosphorescent dopants as cited in JP2003-515897 A (patent document 1).

Patent document 1: JP2003-515897 A
Patent document 2: JP2001-313178 A
Patent document 3: JP2002-305083 A
Patent document 4: JP2002-352957 A
Patent document 5: JP11-162650 A
Patent document 6: JP11-176578 A In the development of organic EL devices, CBP that is a carbazole compound is proposed as a host material for use in the light-emitting layer as cited in JP2001-313178 A. However, the use of CBP as a host material for tris(2-phenylpyridine)iridium complex (hereinafter referred to as Ir(ppy)3) that is a phosphorescent material emitting green light destroys the balanced injection of electrical charges as CBP has a property of facilitating the flow of hole and obstructing the flow of electrons and excess holes flow out to the side of the electron-transporting layer to lower the luminous efficiency from Ir(ppy)3.

As a means to solve the aforementioned problem, a hole-blocking layer may be disposed between the light-emitting layer and the electron-transporting layer. The hole-blocking layer accumulates holes efficiently in the light-emitting layer thereby improving the probability of recombination of holes and electrons in the light-emitting layer and enhancing the luminous efficiency. Examples of the materials currently in general use for the hole-blocking layer include 2,9-dimethyl-4,7-diphenyl-1,10-phenanthroline (hereinafter referred to as BCP) and p-phenylphenolato-bis(2-methyl-8-quinolinolato-N1,O8)aluminum (hereinafter referred to as BAlq). A hole-blocking material such as this can prevent electrons and holes from recombining in the electron-transporting layer. However, BCP lacks reliability as a hole-blocking material as it tends to crystallize easily at room temperature and a device comprising BCP shows an extremely short operating life. On the other hand, BAlq has a Tg of approximately 100° C. and a device comprising BAlq is reported to show a relatively long operating life, but the hole-blocking ability of BAlq is not sufficient and the luminous efficiency from Ir(ppy)3 drops.

On the other hand, 3-phenyl-4-(1'-naphthyl)-5-phenyl-1,2,4-triazole (hereinafter referred to as TAZ) is also proposed as a host material for a phosphorescent organic EL device as cited in JP2002-352957 A; however, TAZ has a property of facilitating the flow of electrons and obstructing the flow of holes and the light-emitting range is displaced toward the side of the hole-transporting layer. Hence, it is conceivable that the luminous efficiency from Ir(ppy)3 may fall depending upon the compatibility of the material used for the hole-transporting layer with Ir(ppy)3. For example, 4,4'-bis[N-(1-naphthyl)-N-phenylamino]biphenyl (hereinafter referred to as NPB) that is a material most widely used in the hole-transporting layer for its excellent performance, high reliability, and long operating life shows poor compatibility with Ir(ppy)3 and energy transition occurs from Ir(ppy)3 to NPB to lower the luminous efficiency.

The patent documents JP11-162650 A and JP11-176578 A disclose indolocarbazole compounds, but they disclose none of the compounds of this invention. Further, the disclosed indolocarbazole compounds are recommended for use as a host-transporting material and their stability is highly regarded, but the documents do not teach the use as a phosphorescent host material.

DISCLOSURE OF THE INVENTION

Problems to be Solved by the Invention

In applications of organic EL devices to display devices such as flat panel displays, it is necessary to improve the luminous efficiency of the device and, at the same time, to fully secure the driving stability of the device. Under the existing circumstances, an object of this invention is to provide an organic EL device which performs at high efficiency with good driving stability and can be put to practical use and to provide a compound for use therein.

Means to Solve the Problems

The inventors of this invention have conducted intensive studies, found that the aforementioned problems can be solved by using a compound having a specific indolocarbazole skeleton in an organic EL device, and completed this invention.

In this invention, a compound for use in an organic electroluminescent is represented by the following general formula (1)

wherein,
Z is a linking group consisting of a non-condensed substituted or unsubstituted aromatic hydrocarbon group or a non-condensed substituted or unsubstituted aromatic heterocyclic group,
n is an integer of 2 or greater, and
Y is a group represented by the following formula (1a);

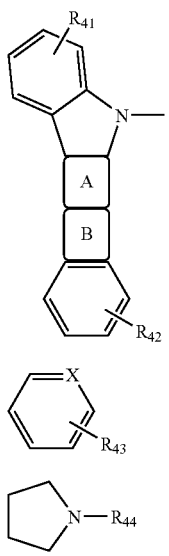

wherein,
ring A is an aromatic or heterocyclic ring condensed with the adjacent rings and represented by formula (1b),
ring B is a heterocyclic ring condensed with the adjacent rings and represented by formula (1c),
X is carbon or nitrogen,
$R_{43}$ is hydrogen, a non-condensed substituted or unsubstituted aromatic hydrocarbon group, a non-condensed substituted or unsubstituted aromatic heterocyclic group, or a ring condensed with the X-containing ring,
$R_{44}$ is a non-condensed substituted or unsubstituted aromatic hydrocarbon group or a non-condensed substituted or unsubstituted aromatic heterocyclic group,
each of $R_{41}$ and $R_{42}$ is hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, a substituted or unsubstituted aromatic hydrocarbon group, or a substituted or unsubstituted heterocyclic group.

A compound represented by general formula (1) wherein Y is represented by the following formula (1d) provides an excellent compound for use in an organic electroluminescent device. Or, so does a compound represented by general formula (1) wherein n is 2, 3, or 4.

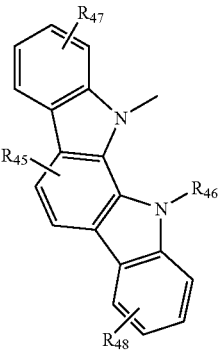

wherein,
$R_{45}$ is hydrogen, a non-condensed substituted or unsubstituted aromatic hydrocarbon group or a non-condensed substituted or unsubstituted aromatic heterocyclic group,
$R_{46}$ has the same meaning as $R_{44}$, and
each of $R_{47}$ and $R_{48}$ independently has the same meaning as $R_{41}$.

The compounds for use in the organic electroluminescent device of this invention represented by general formula (1) comprise a compound represented by the following general formula (2) or (3).

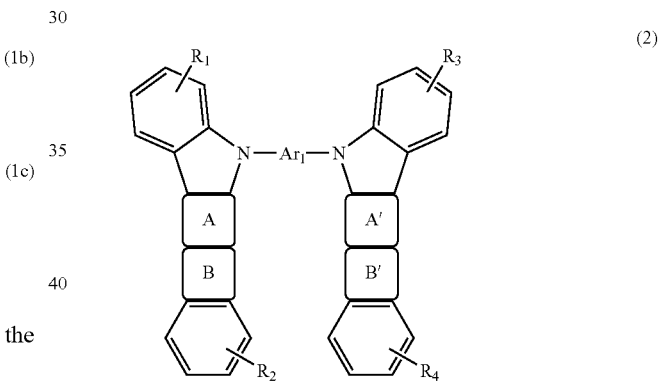

wherein,
each of ring A and ring A' is an aromatic ring condensed with the adjacent rings and represented by formula (2a) and
each of ring B and ring B' is a heterocyclic ring condensed with the adjacent rings and represented by formula (2b).

(3)

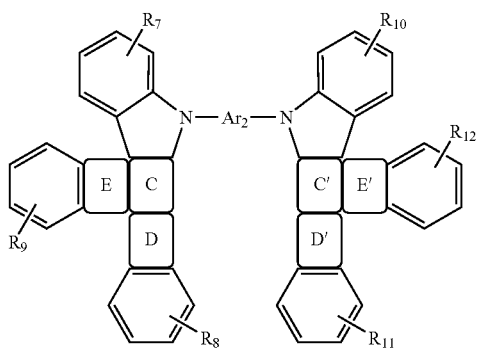

(3a)

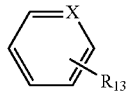

(3b)

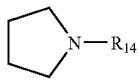

(3c)

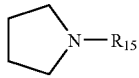

wherein, each of ring C and ring C' is an aromatic ring condensed with the adjacent rings and represented by formula (3a), each of ring D and ring D' is a heterocyclic ring condensed with the adjacent rings and represented by formula (3b), and each of ring E and ring E' is a heterocyclic ring condensed with the adjacent rings and represented by formula (3c).

Further, the compounds for use in the organic electroluminescent devices of this invention comprise a compound represented by the following general formula (4) or (5).

(4)

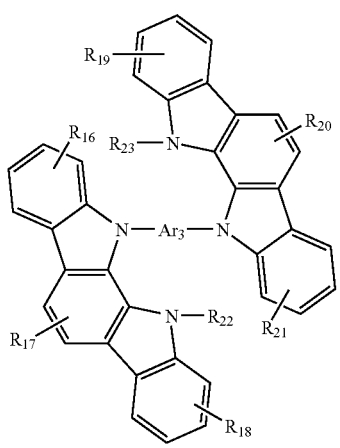

(5)

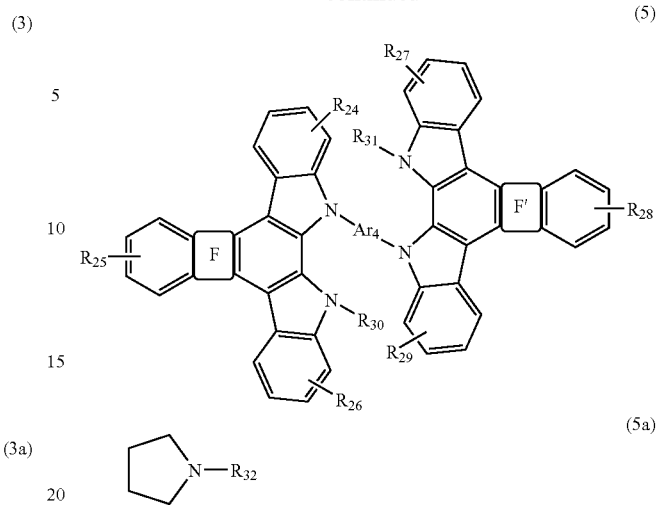

(5a)

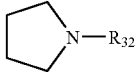

wherein, each of ring F and ring F' is a heterocyclic ring condensed with the adjacent rings and represented by formula (5a).

Any of the compounds represented by the aforementioned general formulas (2) to (5) and formulas (2a) to (2c), (3a) to (3c), and (5a) wherein each of rings A, A', C, and C' is a benzene ring, each of $R_6$, $R_{14}$, $R_{15}$, $R_{22}$, $R_{23}$, $R_{30}$, $R_{31}$, and $R_{32}$ is a substituted or unsubstituted phenyl or pyridyl group, and each of to $R_4$, $R_7$ to $R_{12}$, $R_{16}$ to $R_{21}$, and $R_{24}$ to $R_{29}$ is hydrogen or a phenyl group provides an excellent compound for use in an organic electroluminescent device.

The symbols in the aforementioned general formulas (1) to (5) and formulas (1a) to (1d), (2a) to (2c), (3a) to (3c), and (5a) have the following meaning:

X is carbon or nitrogen; each of $R_5$, $R_{13}$, $R_{17}$, $R_{20}$, and $R_{45}$ is independently hydrogen, a non-condensed substituted or unsubstituted aromatic hydrocarbon group, or a non-condensed substituted or unsubstituted aromatic heterocyclic group, each of $R_6$, $R_{14}$, $R_{15}$, $R_{22}$, $R_{23}$, $R_{30}$, $R_{31}$, $R_{32}$, $R_{44}$, and $R_{46}$ is independently a non-condensed substituted or unsubstituted aromatic hydrocarbon group or a non-condensed substituted or unsubstituted aromatic heterocyclic group, each of $Ar_1$ to $Ar_4$ is independently a divalent linking group consisting of a non-condensed substituted or unsubstituted aromatic hydrocarbon group or a non-condensed substituted or unsubstituted aromatic heterocyclic group, and each of $R_1$ to $R_4$, $R_7$ to $R_{12}$, $R_{16}$, $R_{18}$, $R_{19}$, $R_{21}$, $R_{24}$ to $R_{29}$, $R_{41}$, $R_{42}$, $R_{47}$, and $R_{48}$ is independently an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, a substituted or unsubstituted aromatic hydrocarbon group, or a substituted or unsubstituted aromatic heterocyclic group.

Further, this invention relates to an organic electroluminescent device comprising a light-emitting layer disposed between an anode and a cathode piled one upon another on a substrate and the light-emitting layer is characterized by containing a phosphorescent dopant and the aforementioned compound for use in an organic electroluminescent device. This electroluminescent device desirably has a hole-injecting/transporting layer disposed between the anode and the light-emitting layer and an electron-injecting/transporting layer disposed between the cathode and the light-emitting layer. Or, a hole-blocking layer is desirably disposed between the light-emitting layer and the electron-injecting/transporting layer.

According to this invention, one or more of the compounds represented by the aforementioned general formula (1), preferably by general formulas (2) to (5), are used in at least one of the organic layers in the organic EL device.

The compound for use in an organic EL device of this invention is represented by the aforementioned general formula (1). In general formula (1), Z is a linking group with a valency of n selected from non-condensed substituted or unsubstituted aromatic hydrocarbon groups or non-condensed substituted or unsubstituted aromatic heterocyclic groups and n is an integer of 2 or greater.

In the case where the linking group Z is an aromatic hydrocarbon group, examples of the aromatic hydrocarbon from which the linking group is derived include benzene, biphenyl, and terphenyl. In the case where Z is an aromatic heterocyclic group, examples of the aromatic heterocyclic compound from which the linking group is derived include pyridine, triazole, diazole, phenylpyridine, phenyltriazole, and triphenyltriazole. In the case where the aromatic hydrocarbon groups or aromatic heterocyclic groups are substituted, preferable examples of the substituent group include an alkyl group of 1 to 6 carbon atoms, a phenyl group, and a pyridyl group. The number of the substituent groups is 0 to 4, preferably 0 to 2.

The group Y is represented by the aforementioned formula (1a). In formula (1a), ring A and ring B are respectively condensed with the adjacent rings. Advantageously, Y is represented by the aforementioned formula (1d).

In the case where each of $R_{41}$ and $R_{42}$ is a substituted or unsubstituted aromatic hydrocarbon group or a substituted or unsubstituted aromatic heterocyclic group, preferable examples of the aromatic hydrocarbon group include a phenyl group and a biphenylyl group and preferable examples of the aromatic heterocyclic group include a pyridyl group. Where these compounds are substituted, examples of the substituent group include an alkyl group of 1 to 6 carbon atoms, a phenyl group, and a pyridyl group. The number of the substituent groups is 0 to 4, preferably 0 to 2.

In the case where $R_{43}$ or $R_{44}$ is an aromatic hydrocarbon group, preferable examples of the aromatic hydrocarbon group include a phenyl group and a biphenylyl group. In the case where $R_{43}$ or $R_{44}$ is an aromatic heterocyclic group, preferable examples of the aromatic heterocyclic group include a pyridyl group. In the case where these groups are substituted, preferable examples of the substituent group include an alkyl group of 1 to 6 carbon atoms, a phenyl group, and a pyridyl group. The number of the substituent groups is 0 to 4, preferably 0 to 2. The group $R_{43}$ may be the aforementioned aromatic hydrocarbon group or aromatic heterocyclic group or it may be hydrogen or a ring condensed with the X-containing six-membered ring of formula (1b), hydrogen or the aforementioned ring being preferred.

In the case where $R_{43}$ is a ring condensed with the X-containing six-membered ring of formula (1b), the ring in question may be a condensed ring. Examples of the condensed rings are rings E and E' in general formula (3) and rings F and F' in general formula (5); namely, the condensed rings are preferably indole rings which may have $R_9$, $R_{12}$, $R_{25}$, or $R_{28}$. In this case, the nitrogen-containing ring of the indole ring condenses with the X-containing six-membered ring.

The compound represented by general formula (1) becomes an indolocarbazole derivative when ring A is a benzene ring and the compound of this invention may be said to be a compound having an indolocarbazole unit. This indolocarbazole unit is the very unit which enhances the hole-transporting ability and n needs to be 2 or greater to enhance this ability still further. Generally, the compounds represented by general formula (1) comprise the compounds represented by general formulas (2) to (5) and it is to be understood that the compounds represented by general formula (1), whenever they are mentioned, include all the compounds represented by general formulas (2) to (5).

The value of n is preferably 2 to 4, more preferably 2 to 3. When n is 5 or greater, the compound in question increases in molecular weight and becomes less disposed to sublimate and this may occasionally interfere with the construction of an electroluminescent device by the vapor deposition process or the purification becomes difficult to perform as a result of polymerization of impurities.

When n is 2, some of the compounds represented by general formula (1) take the form of the compounds represented by general formulas (2) to (5). The symbols appearing in general formulas (2) to (5) and having the same meaning as in general formula (1) preferably express the same groups or rings described in general formula (1).

The organic EL device of this invention comprises a light-emitting layer disposed between an anode and a cathode piled one upon another on a substrate and the light-emitting layer contains a phosphorescent dopant and the aforementioned compound for use in an organic EL device as a host material. It is advantageous to dispose a hole-injecting/transporting layer between the anode and the light-emitting layer and an electron-injecting/transporting layer between the cathode and the light-emitting layer. It is also advantageous to dispose a hole-blocking layer between the light-emitting layer and the electron-injecting/transporting layer.

It is further advantageous to use a compound represented by the aforementioned general formula (1) wherein Y is represented by general formula (1d) or a compound represented by any of general formulas (2) to (5) as a host material in the organic EL device of this invention.

A compound represented by general formula (1) can be prepared readily by a known method, for example, with reference to the synthetic example shown in Tetrahedron, 1991, Vol. 47, No. 37, pp. 7739-7750.

A compound represented by general formula (2) can be prepared by the following reactions.

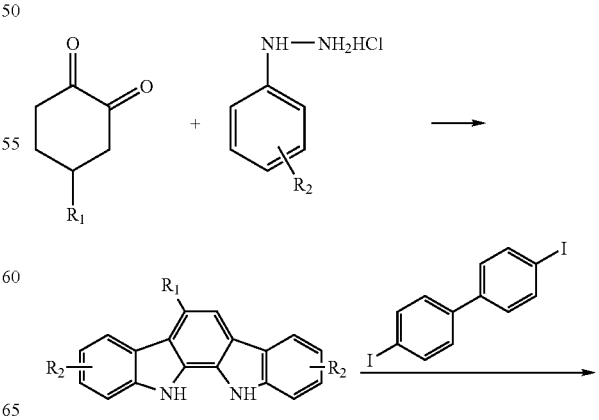

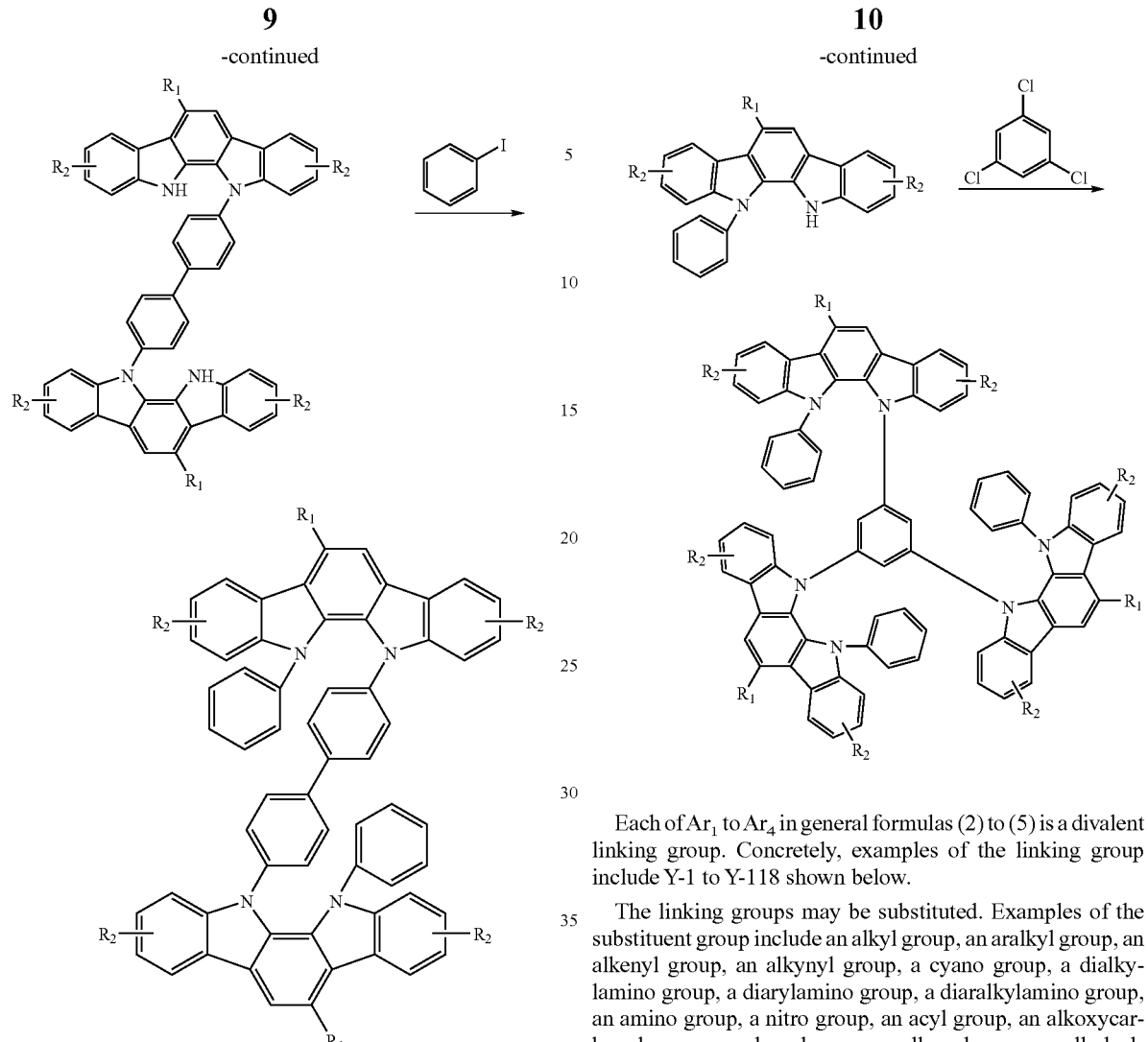

A compound represented by general formula (1) wherein Y is represented by general formula (1d) and n is 3 can be prepared by the following reactions.

Each of Ar₁ to Ar₄ in general formulas (2) to (5) is a divalent linking group. Concretely, examples of the linking group include Y-1 to Y-118 shown below.

The linking groups may be substituted. Examples of the substituent group include an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, a substituted or unsubstituted aromatic hydrocarbon group, or a substituted or unsubstituted aromatic heterocyclic group.

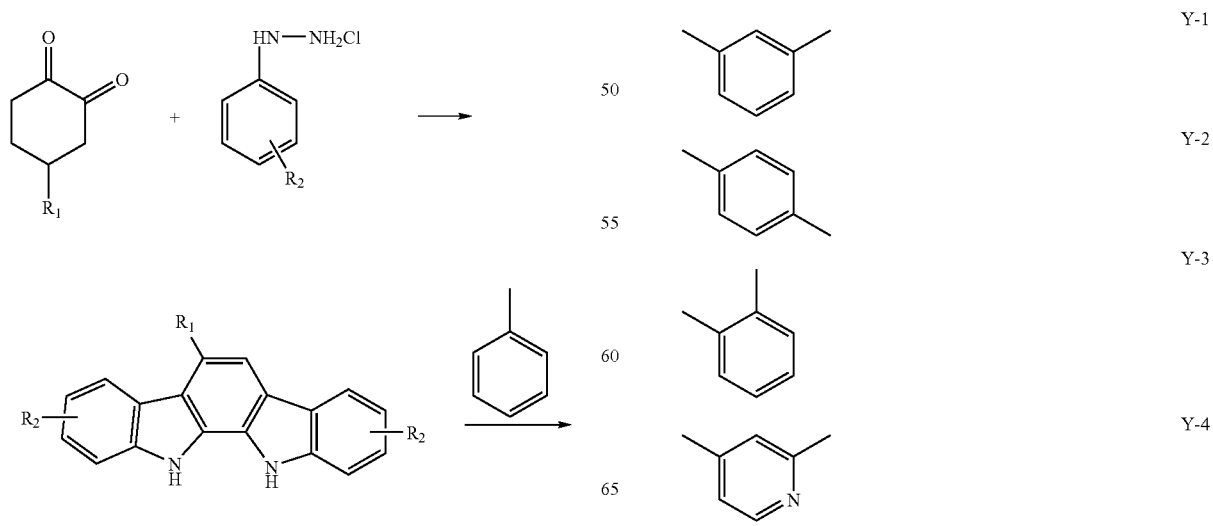

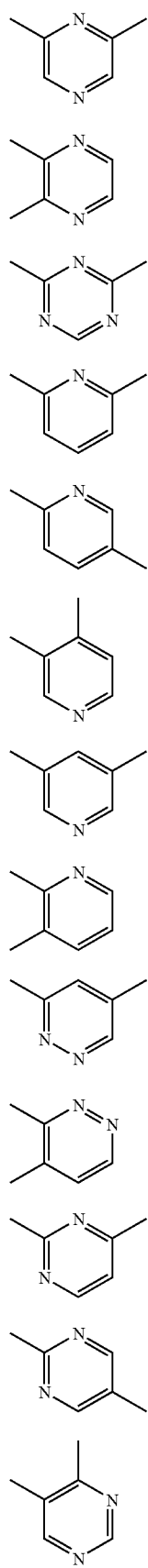
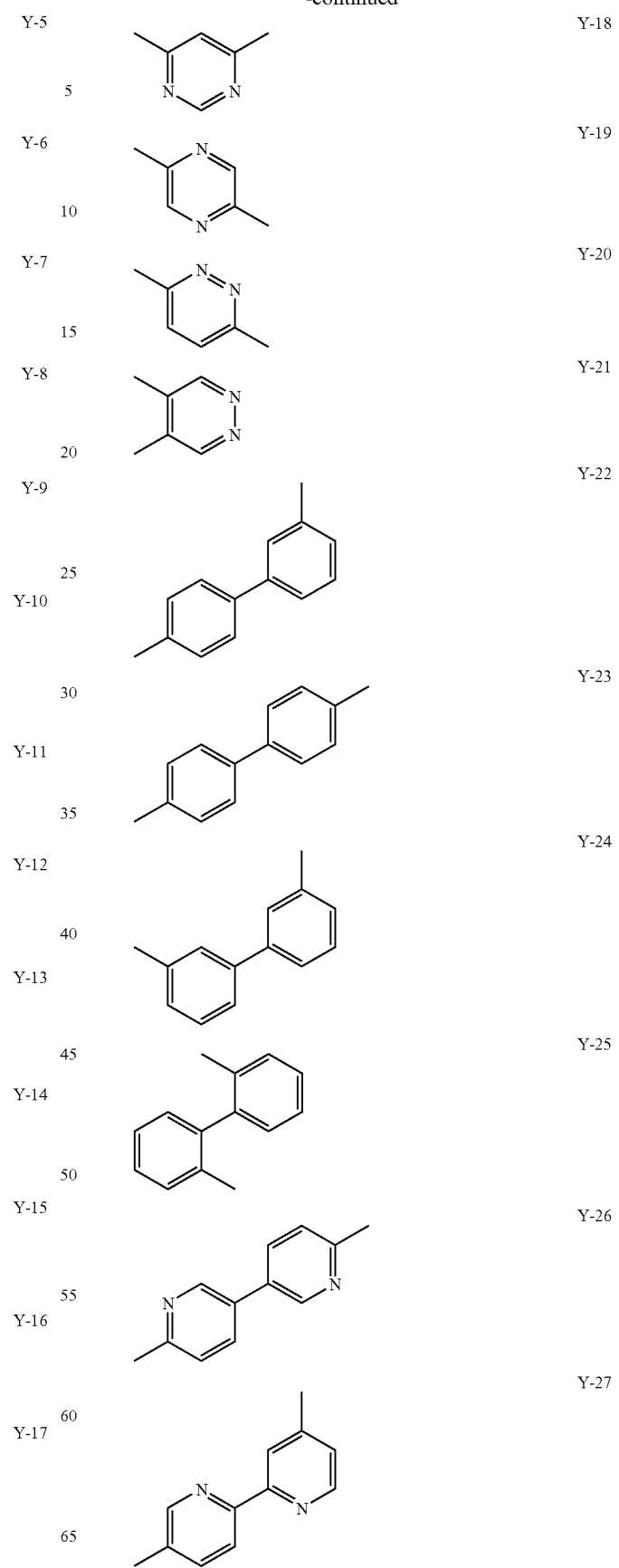

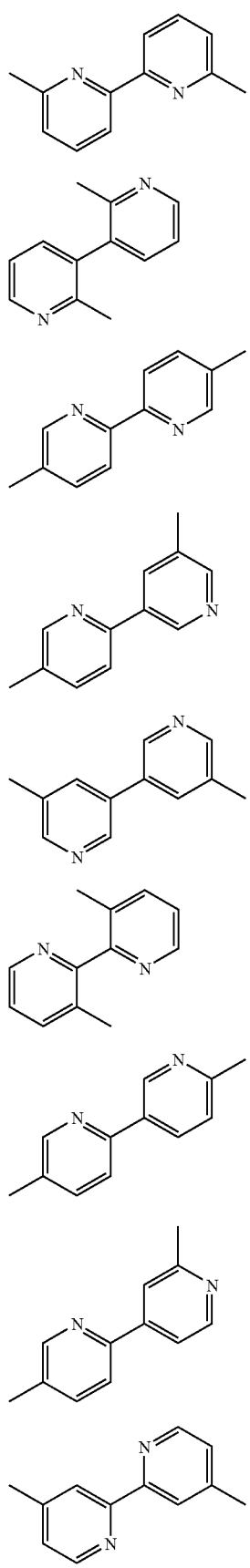
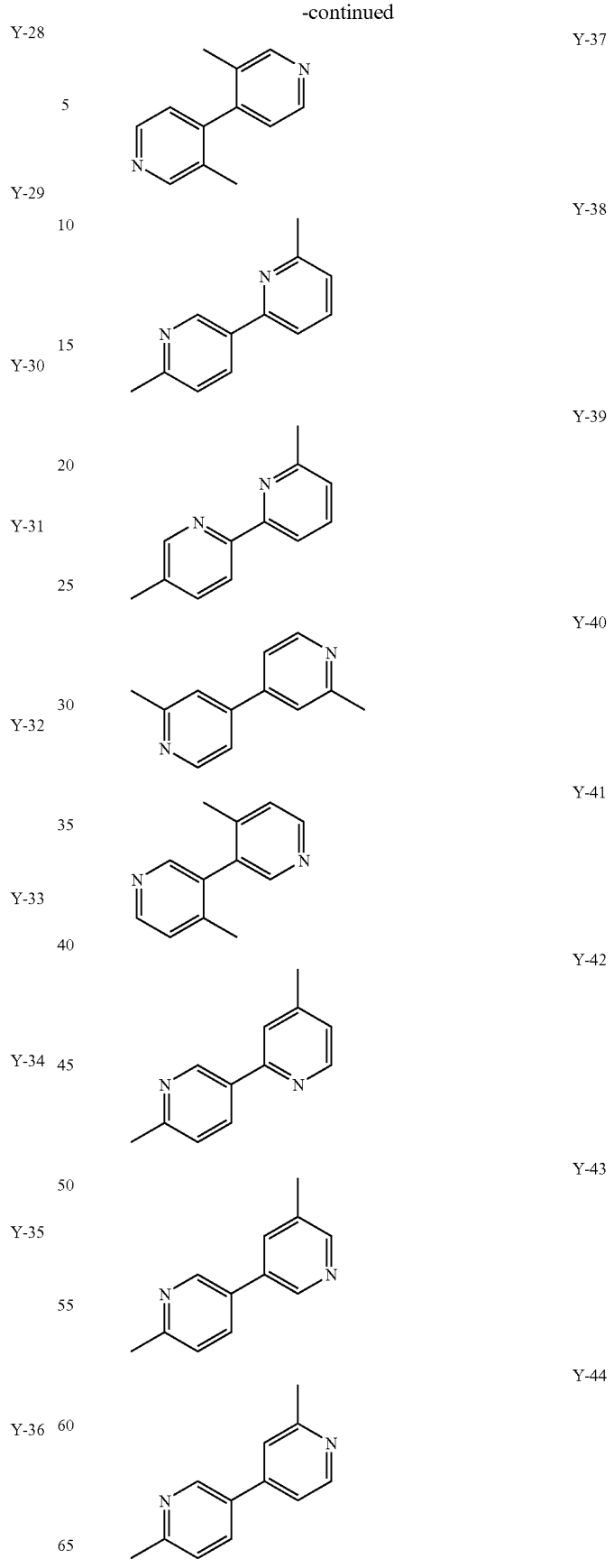

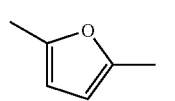
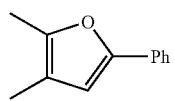
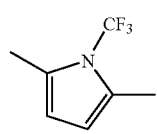
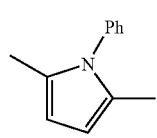
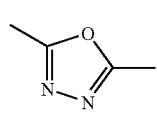
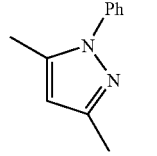
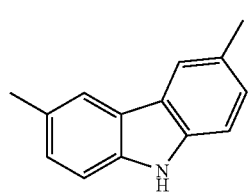
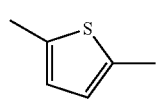
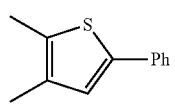
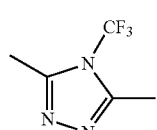
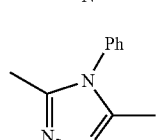
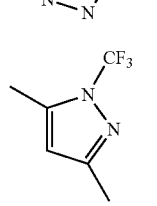
Y-45
Y-46
Y-47
Y-48
Y-49
Y-50
Y-51
Y-52
Y-53
Y-54
Y-55
Y-56
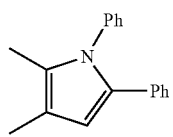
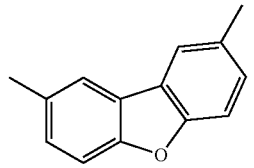
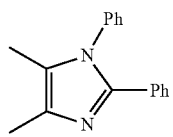
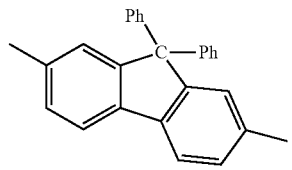
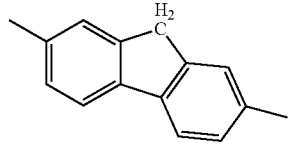
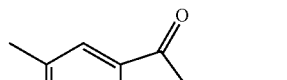
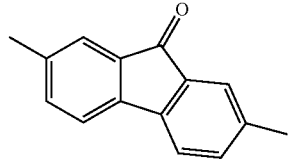
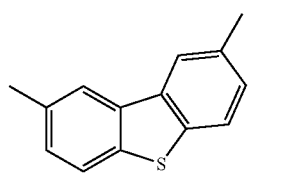
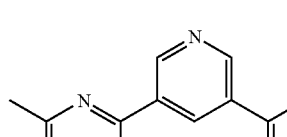
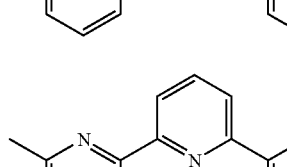
Y-57
Y-58
Y-59
Y-60
Y-61
Y-62
Y-63
Y-64
Y-65

Y-66 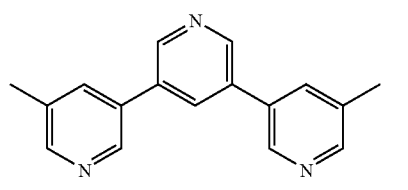
Y-67 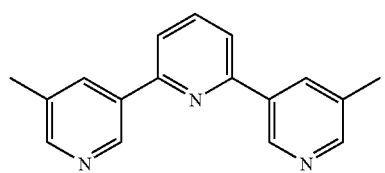
Y-68 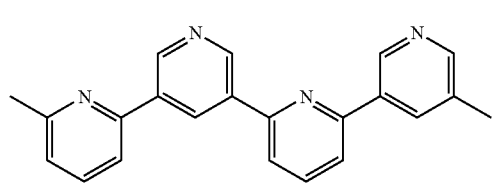
Y-69 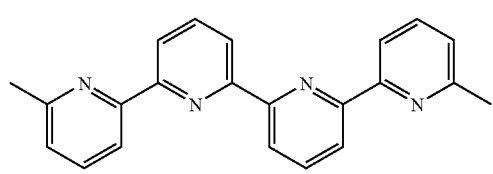
Y-70 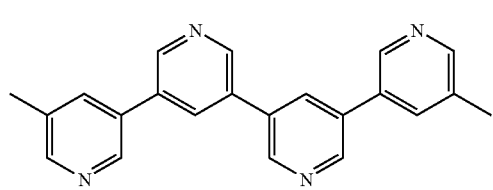
Y-71 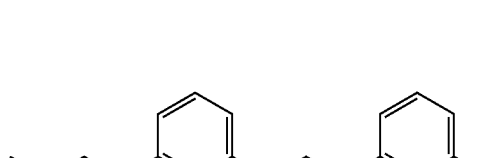
Y-72 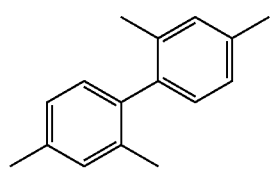
Y-73 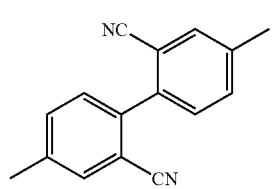
Y-74 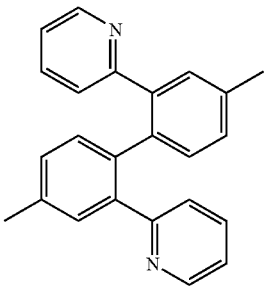
Y-75 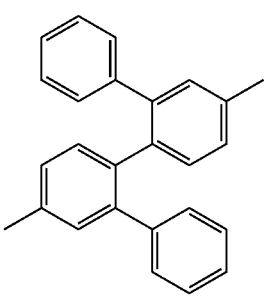
Y-76 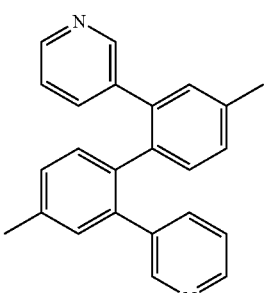
Y-77 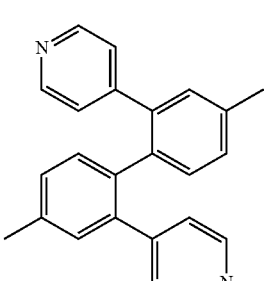
Y-78 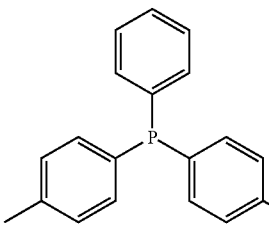
Y-79 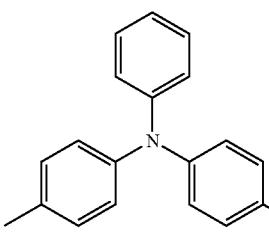

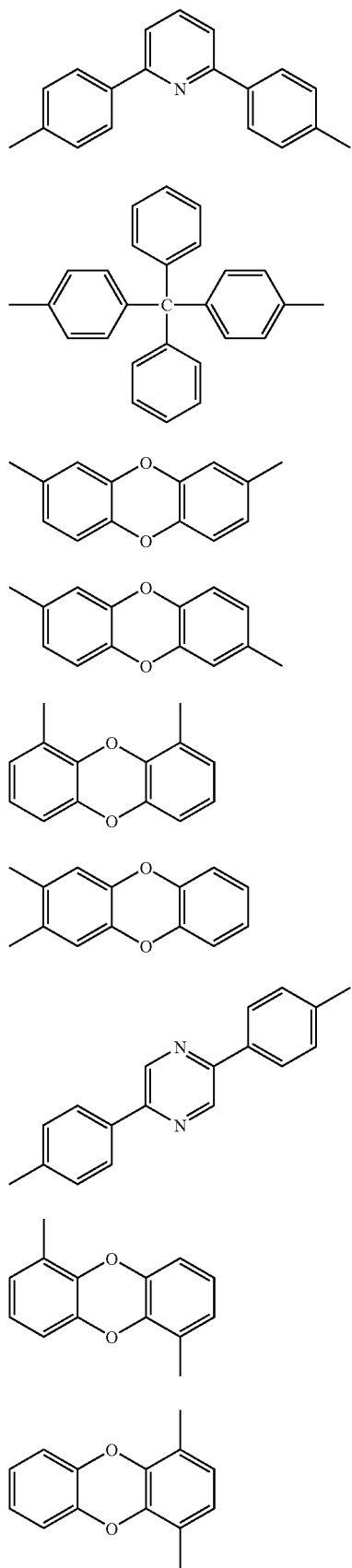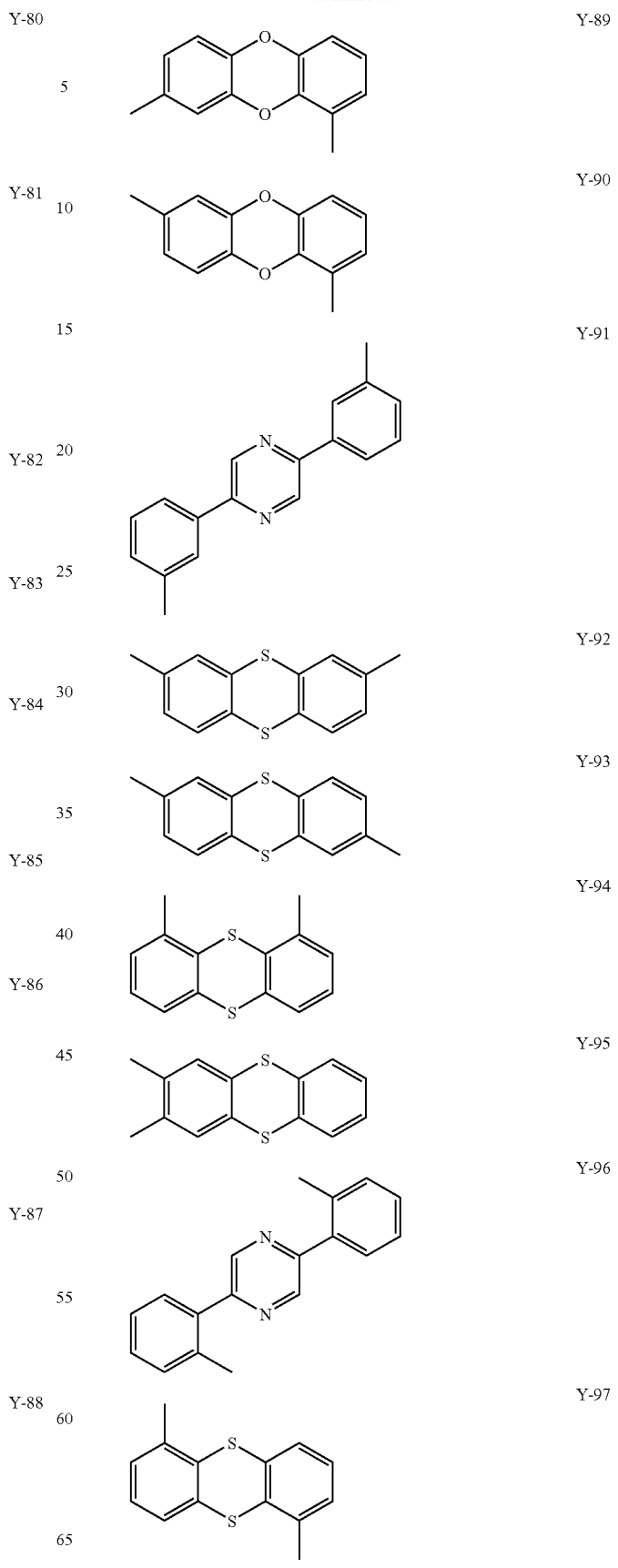

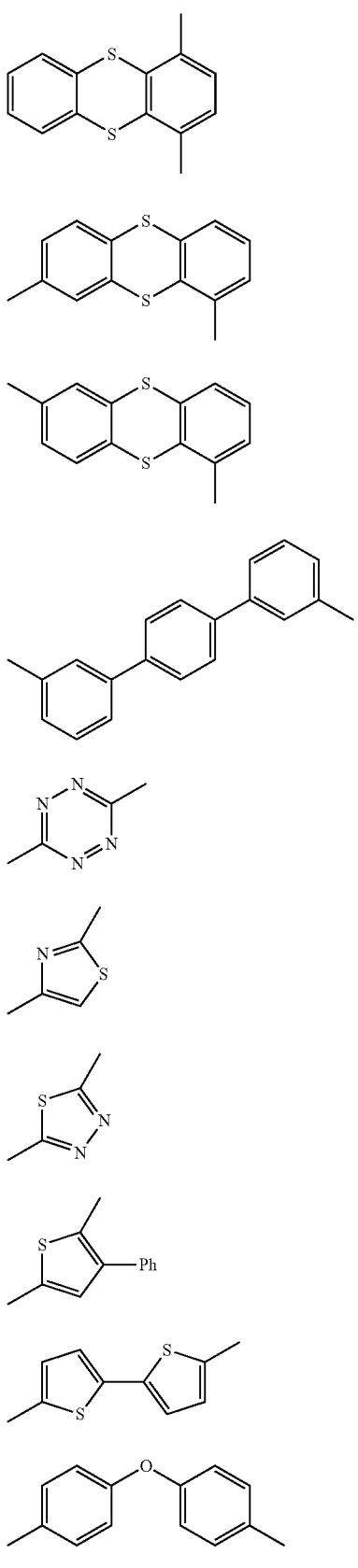
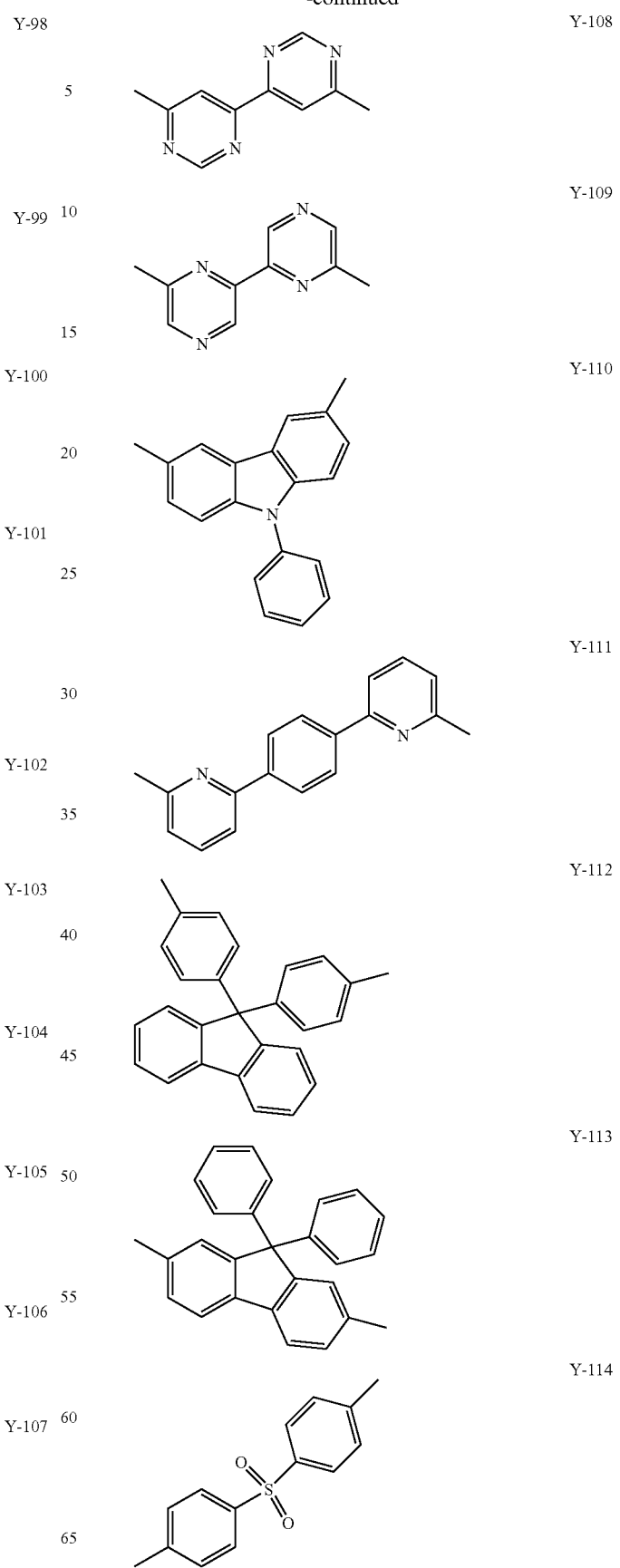

Y-115
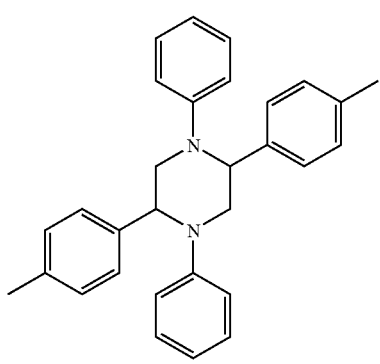
Y-116
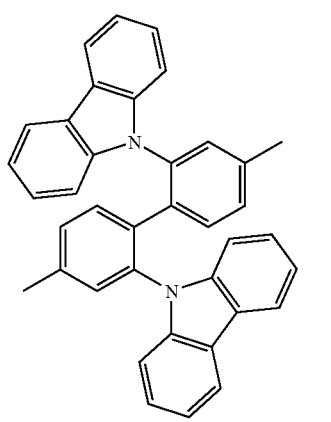
Y-117
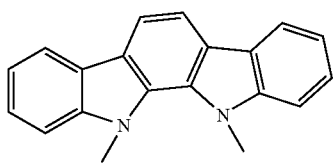
Y-118
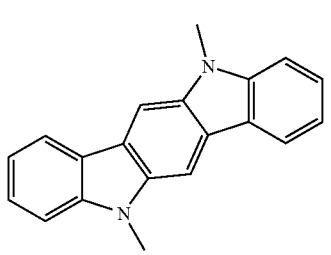
Preferable examples of the substituent group include Z-1 to Z-138 shown below.
Z-1
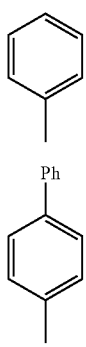
Z-2
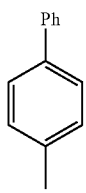
Z-3
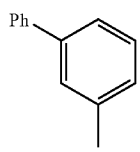
Z-4
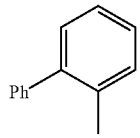
Z-5
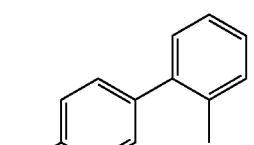
Z-6
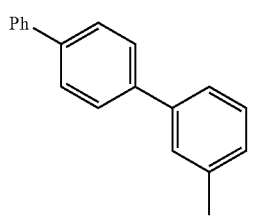
Z-7
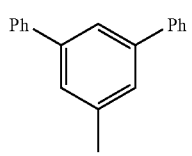
Z-8
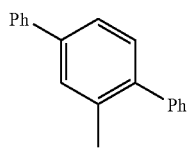
Z-9
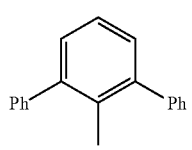
Z-10
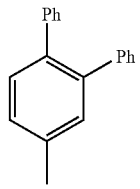
Z-11
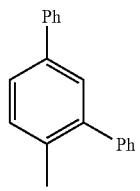

-continued
Z-12 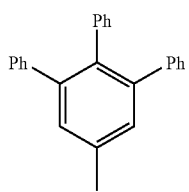
Z-13 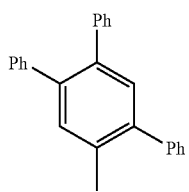
Z-14 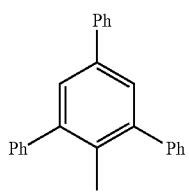
Z-15 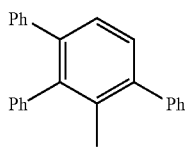
Z-16 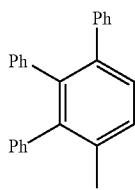
Z-17 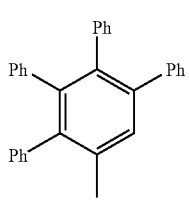
Z-18 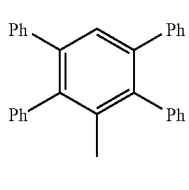
Z-19 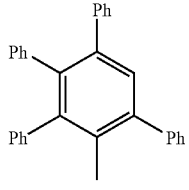
-continued
Z-20 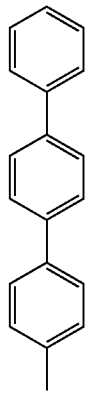
Z-21 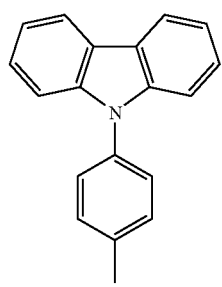
Z-23 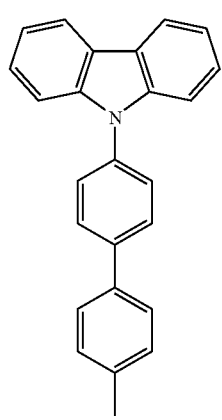
Z-24 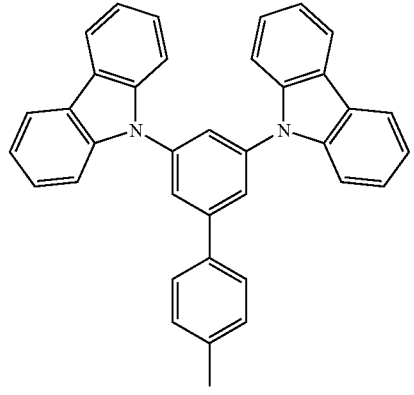

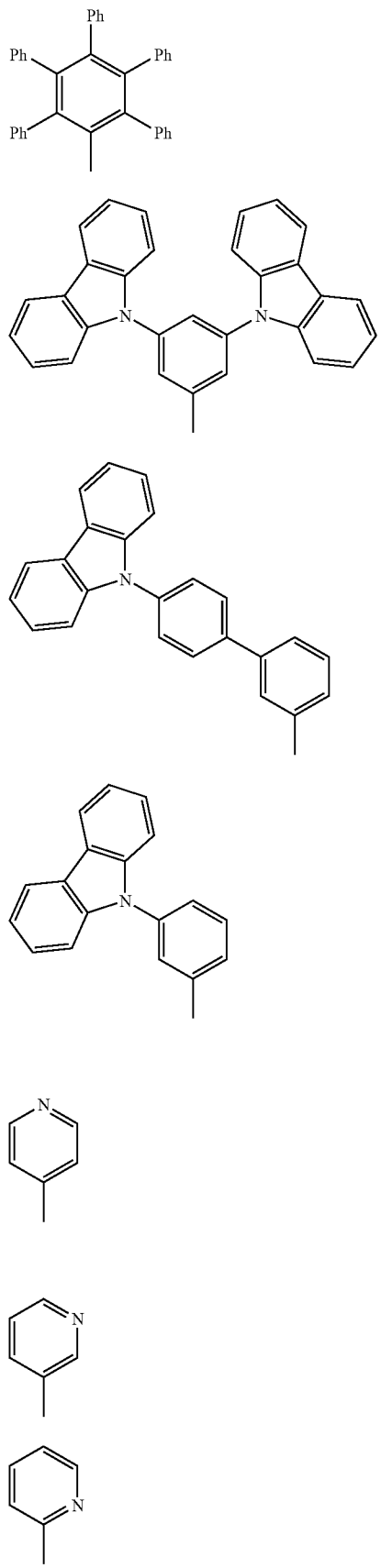
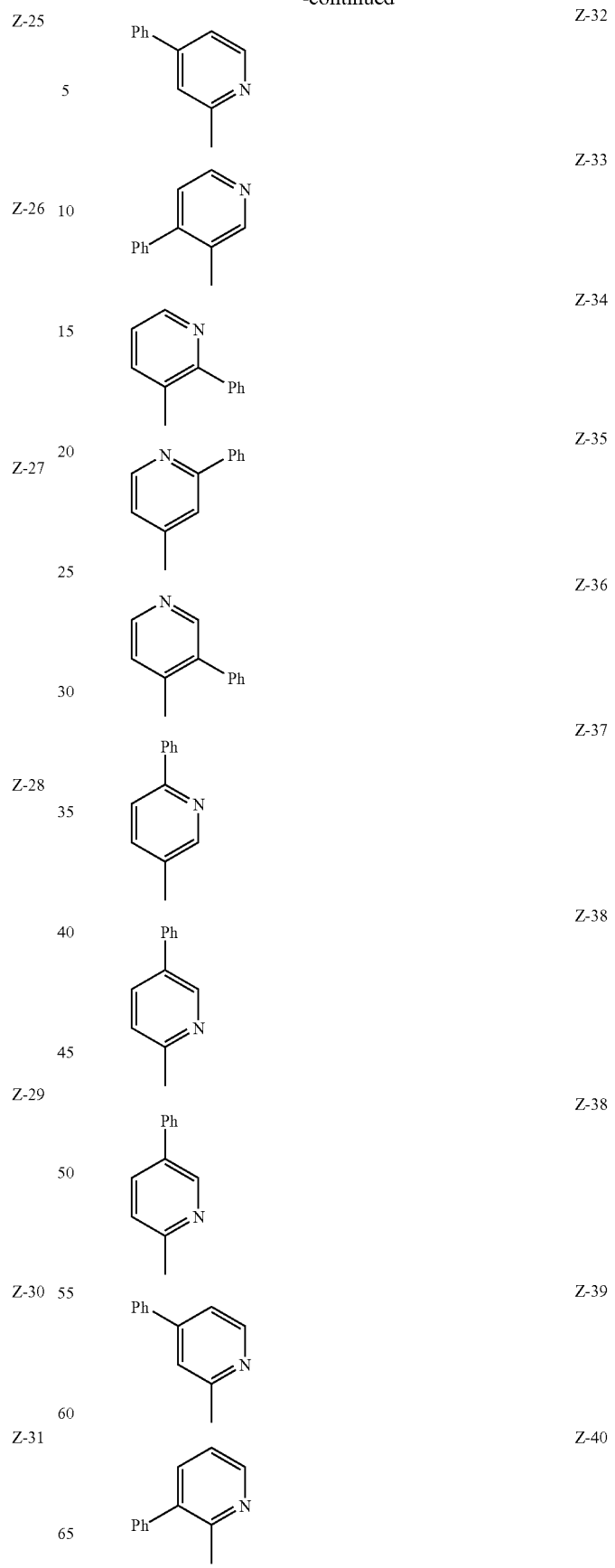

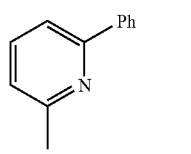 Z-33
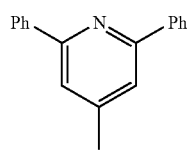 Z-34
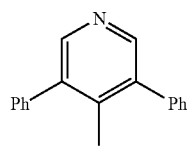 Z-35
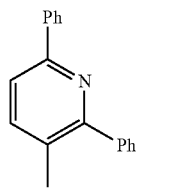 Z-36
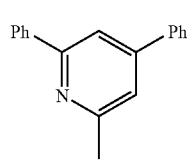 Z-37
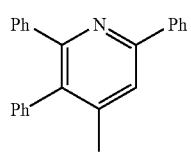 Z-38
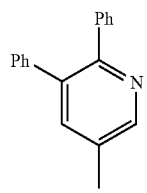 Z-39
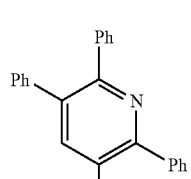 Z-40
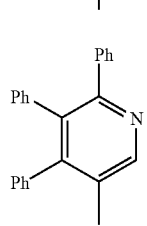 
Z-41
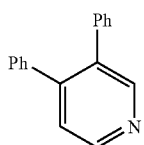 Z-42
Z-43
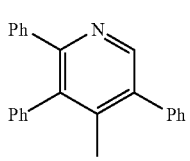 Z-44
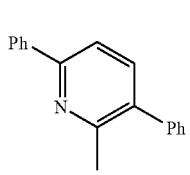 Z-45
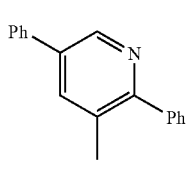 Z-46
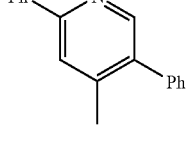 Z-47
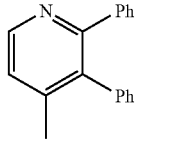 Z-48
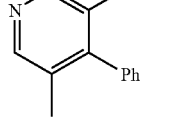 Z-49
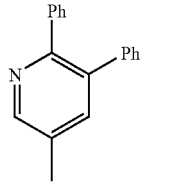 
Z-50
Z-51
Z-52
Z-53
Z-54
Z-55
Z-56
Z-57
Z-58
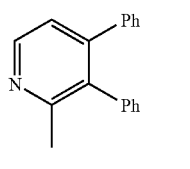

-continued
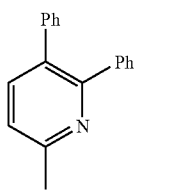
Z-59
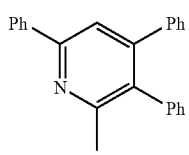
Z-60
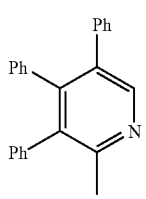
Z-61
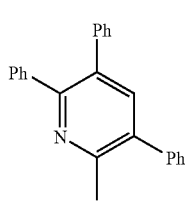
Z-62
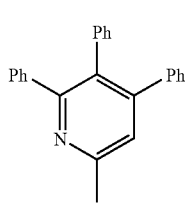
Z-63
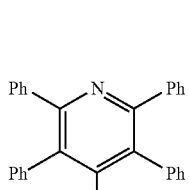
Z-64
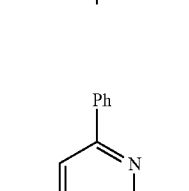
Z-65
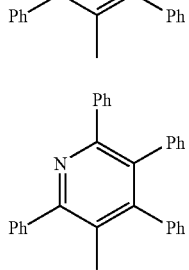
Z-66
-continued
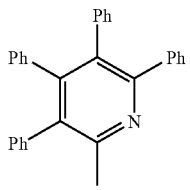
Z-67
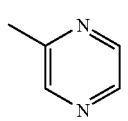
Z-68
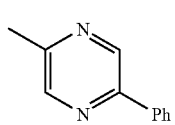
Z-69
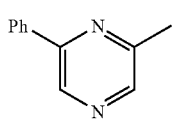
Z-70
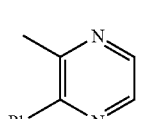
Z-71
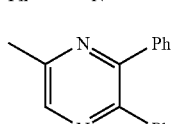
Z-72
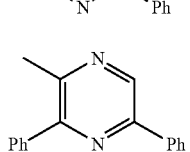
Z-73
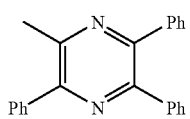
Z-74
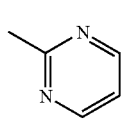
Z-75
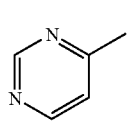
Z-76
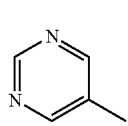
Z-77
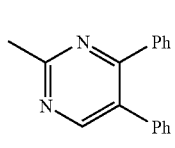
Z-78

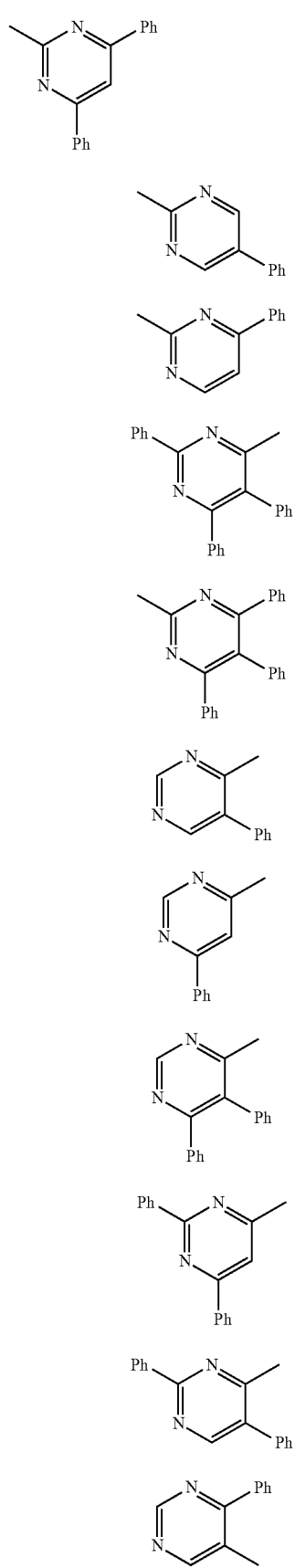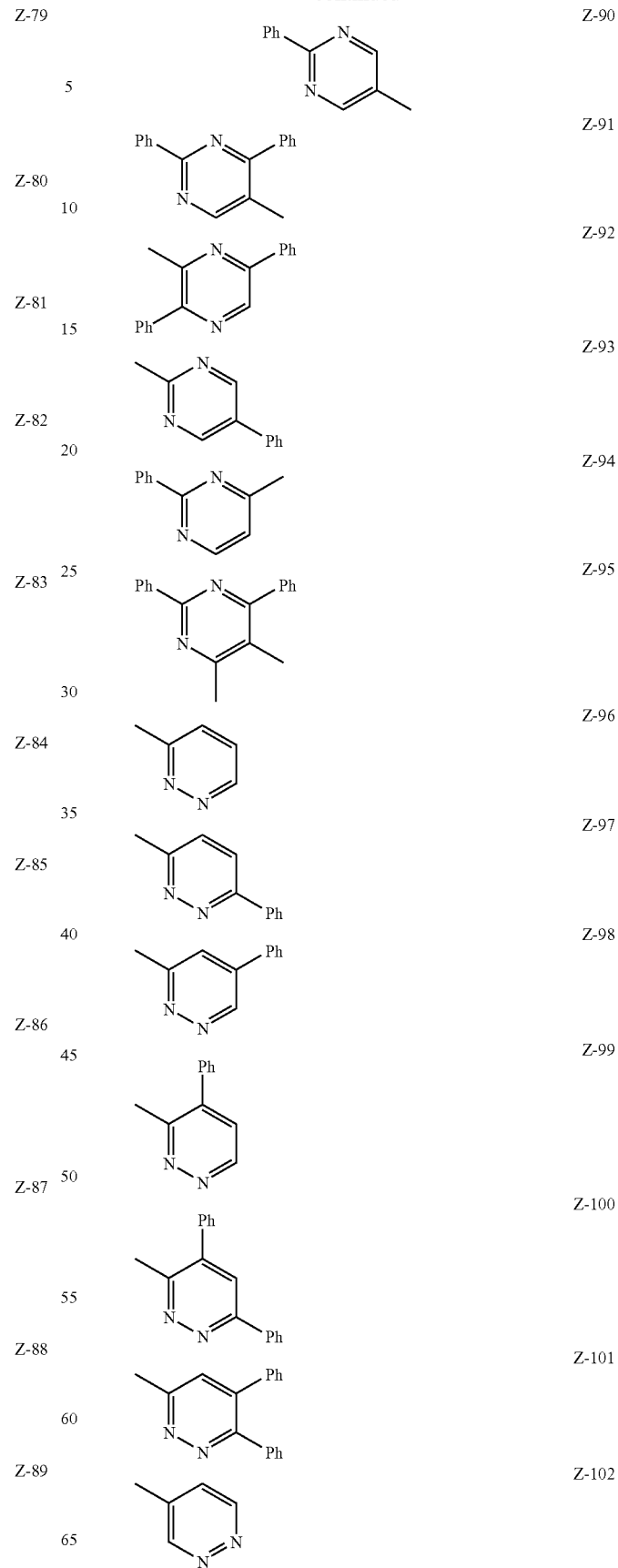

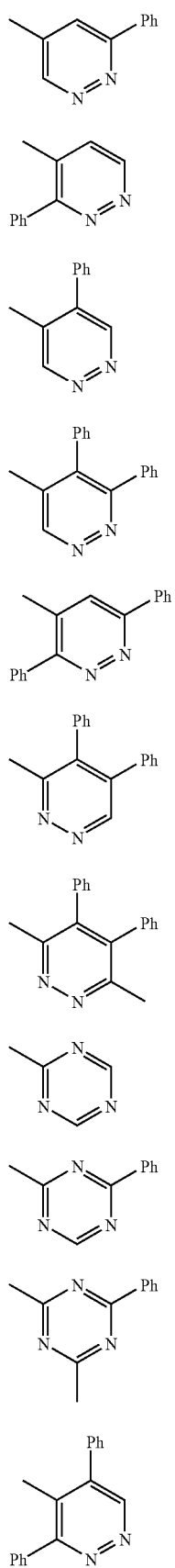
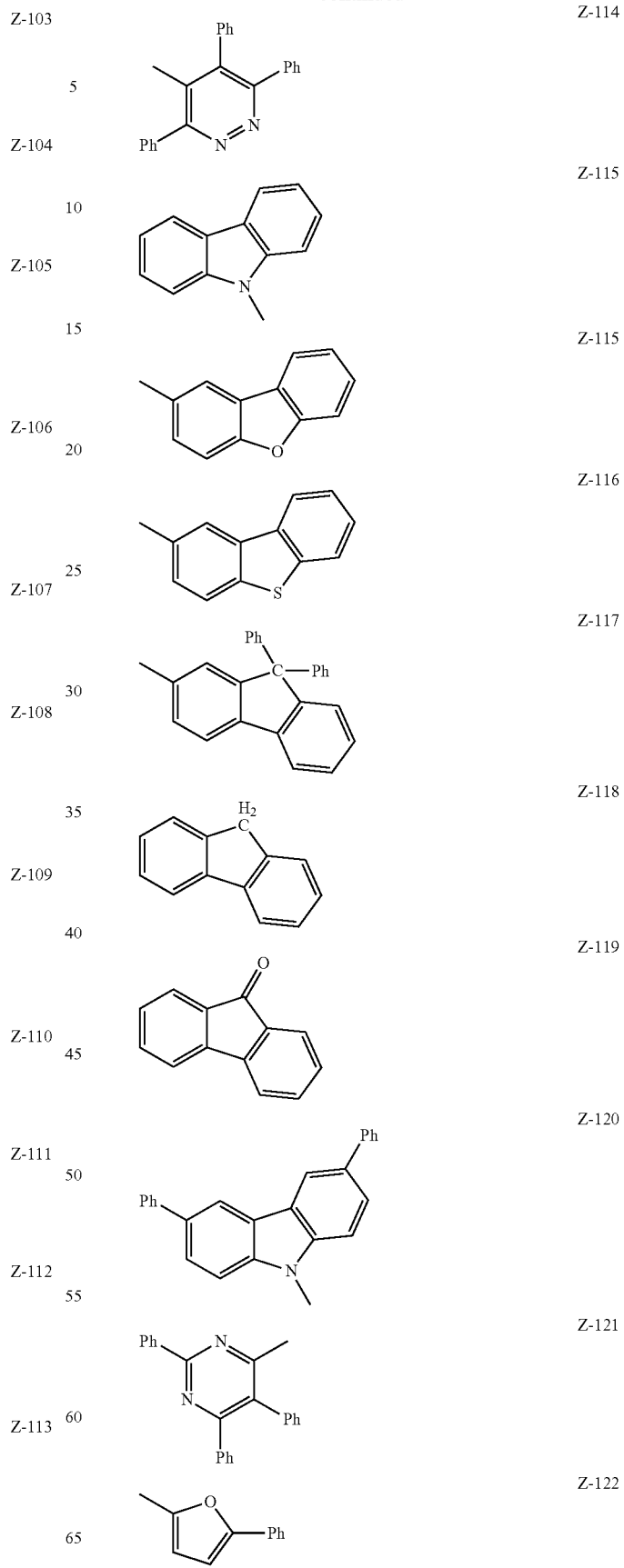

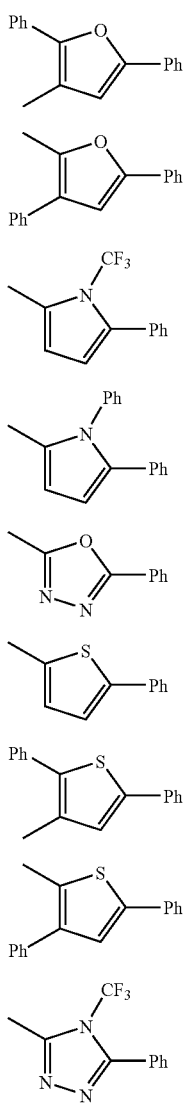
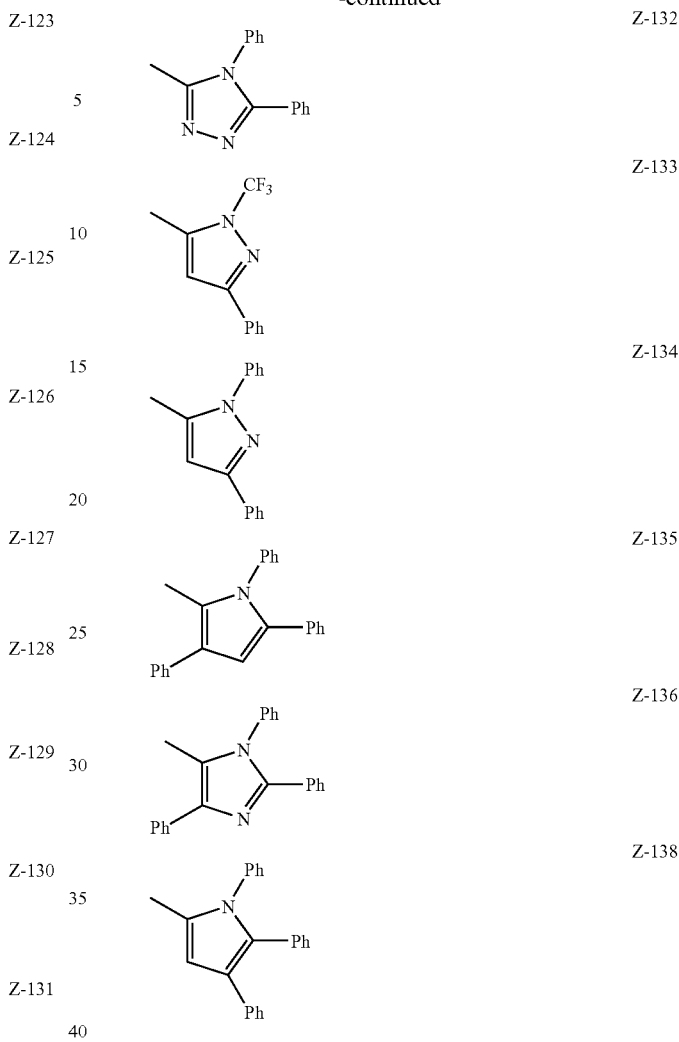
Preferable examples of the compounds represented by the aforementioned general formulas (2) to (5) are shown below, but are not limited thereto.
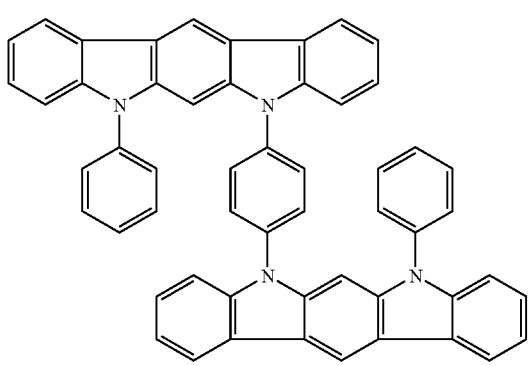
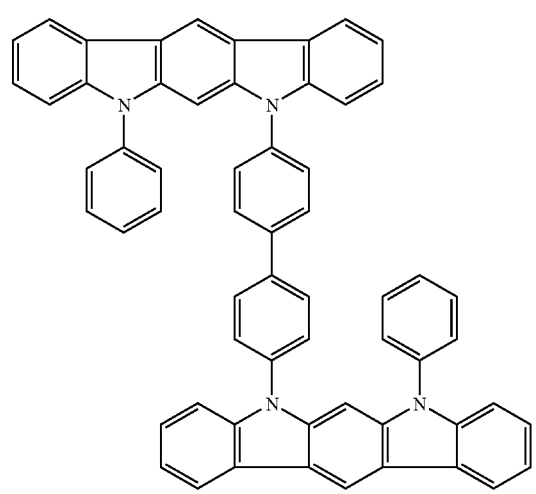

-continued
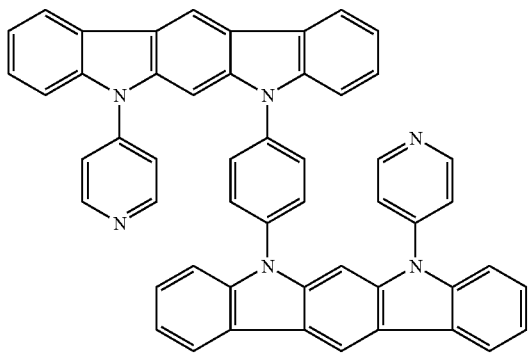
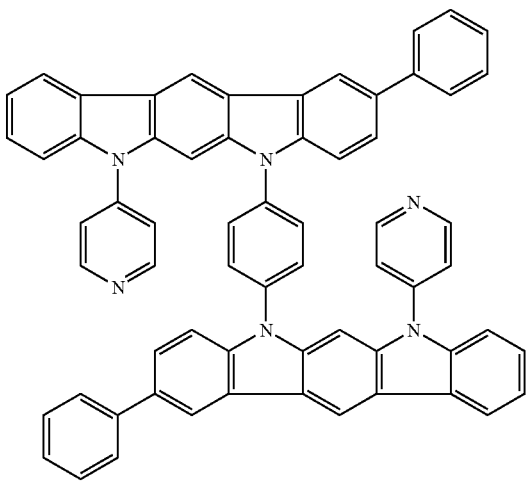
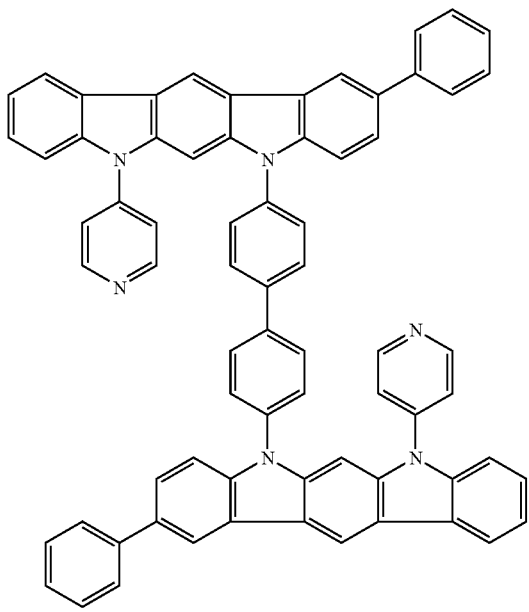
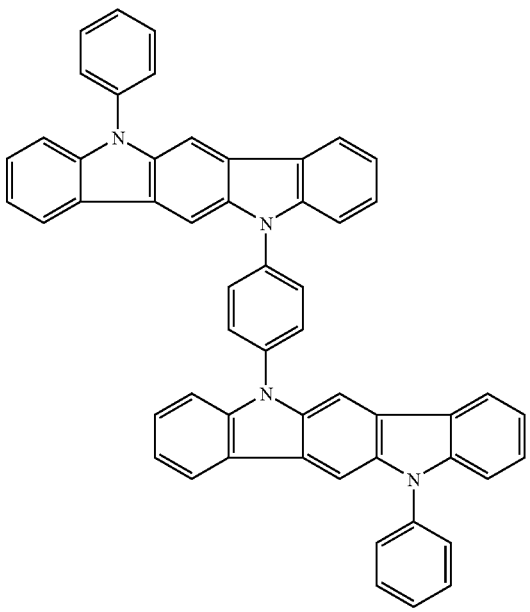

-continued
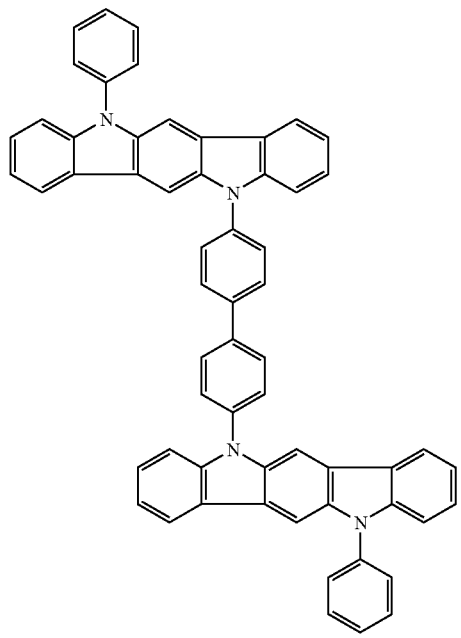
7
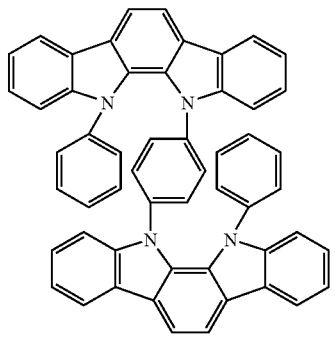
8
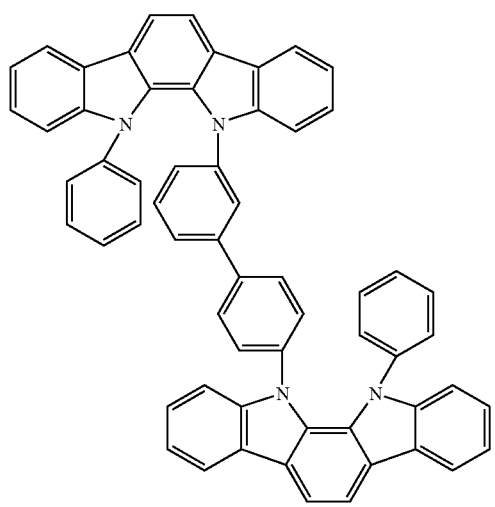
9
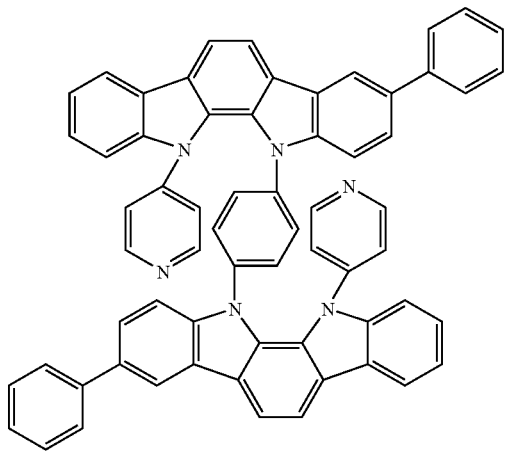
10

-continued
11
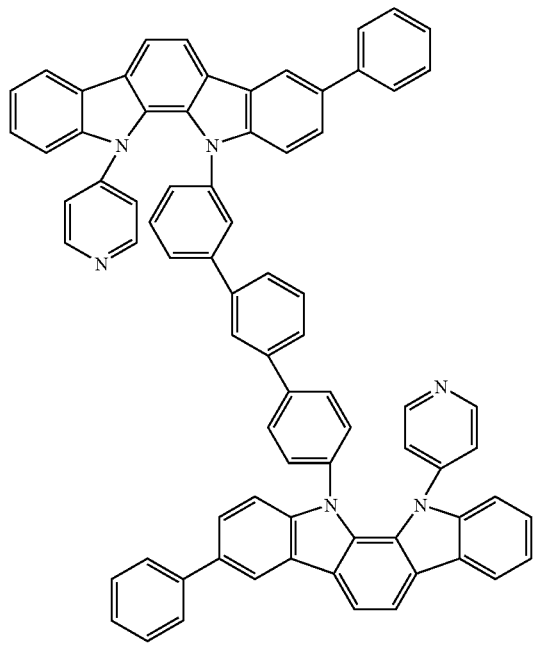
12
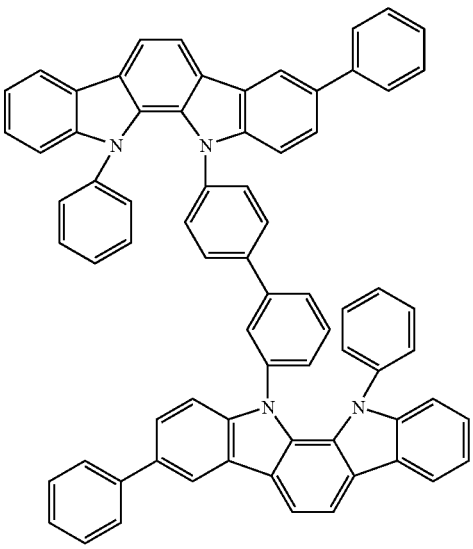
13
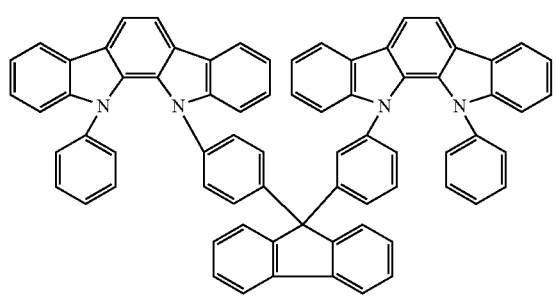
14
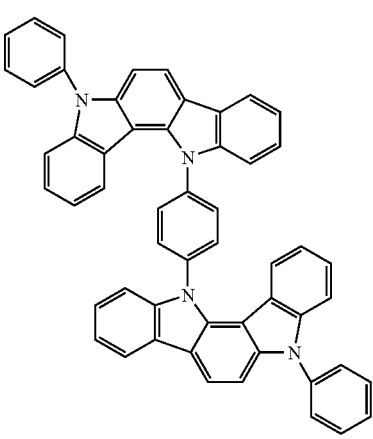

-continued
15
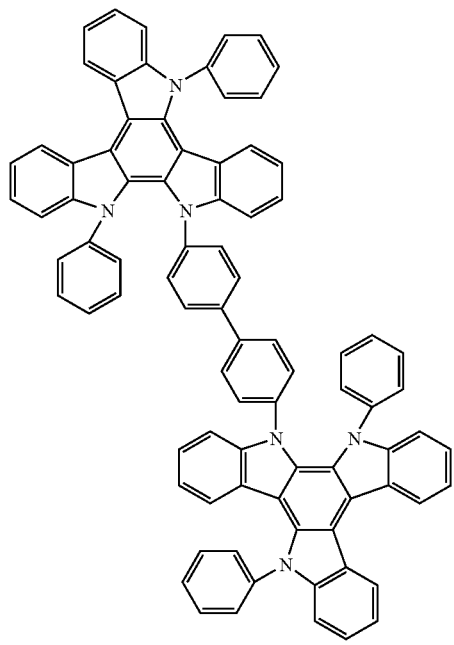
16
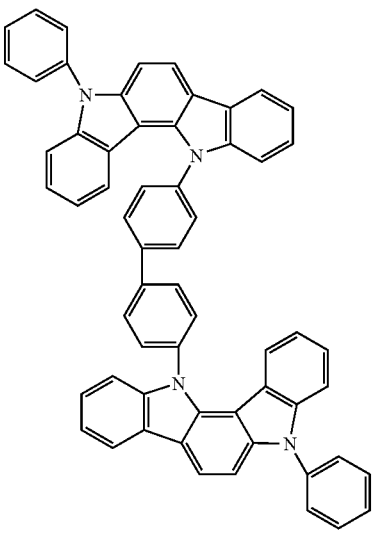
17
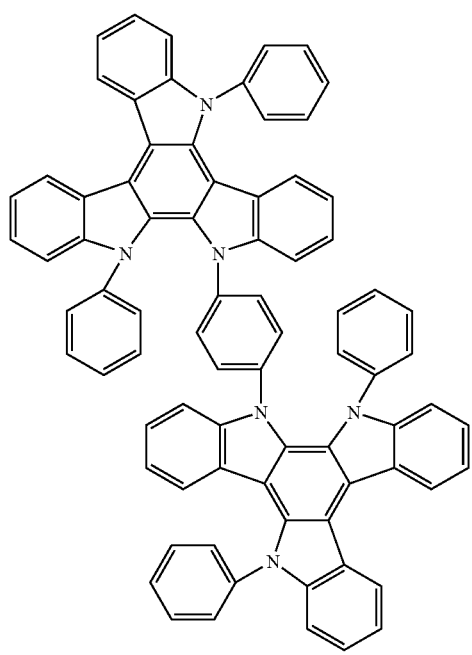
18
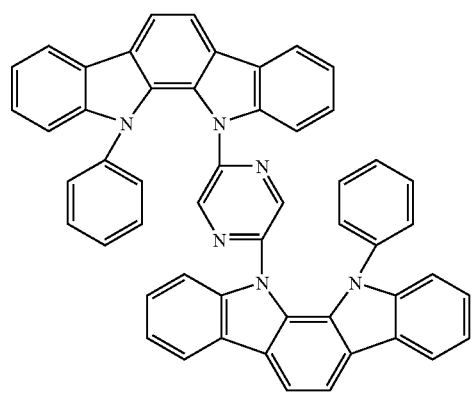

-continued
19
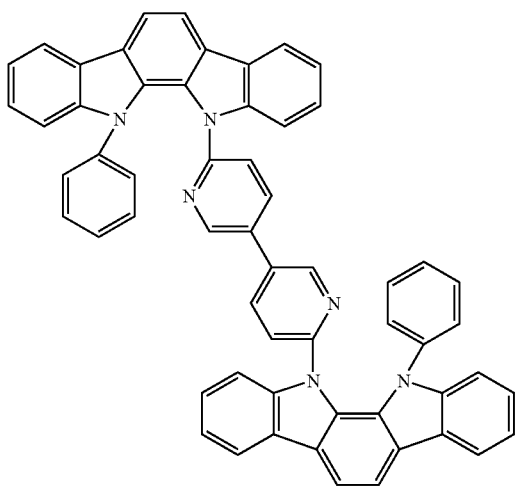
20
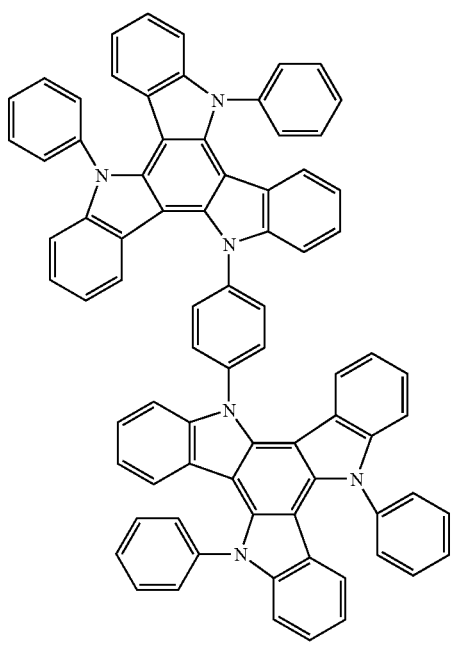
21
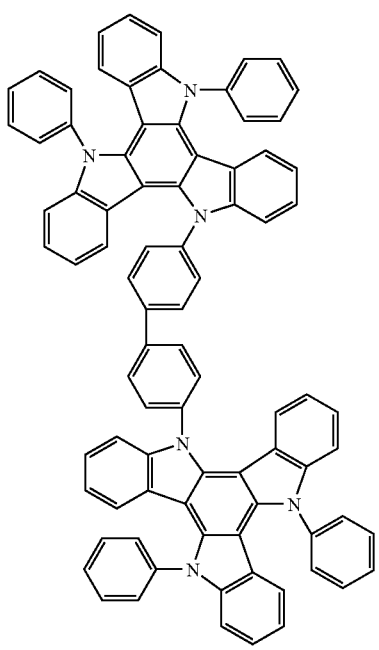
22
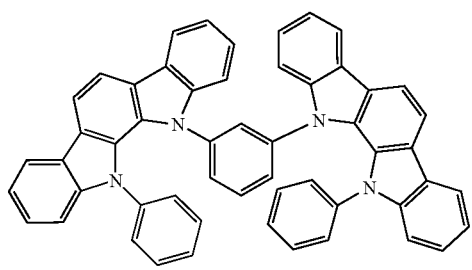
23
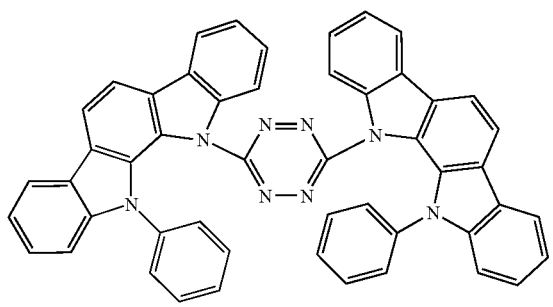
24
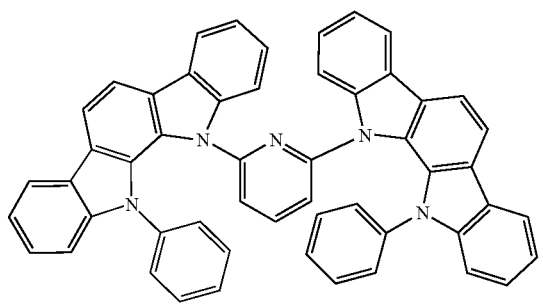

-continued
25
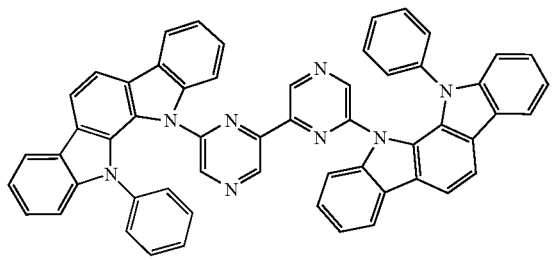
26
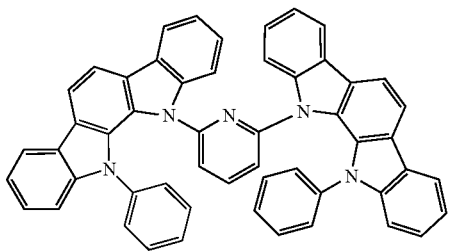
27
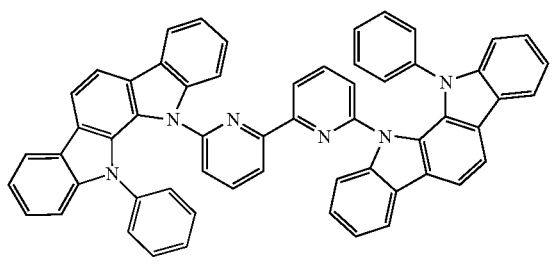
28
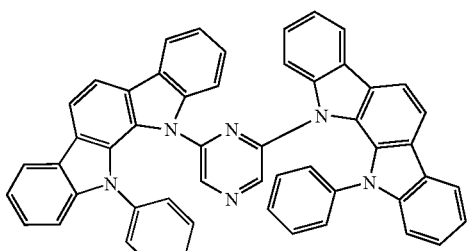
29
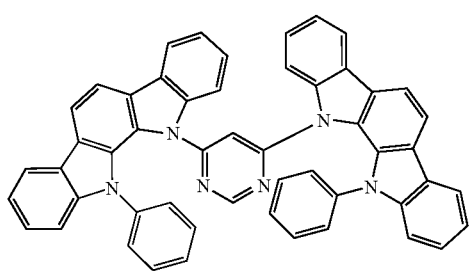
30
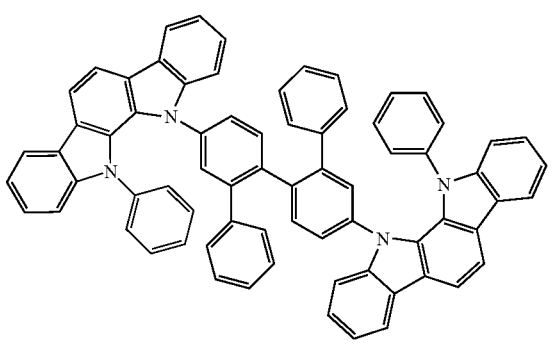
31
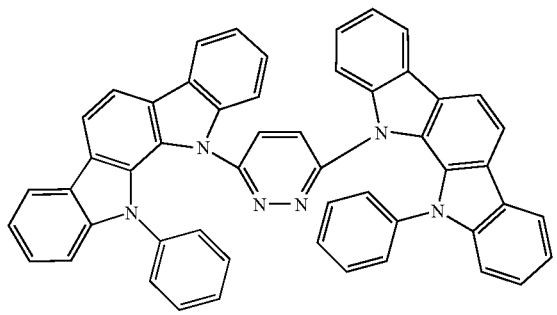
32
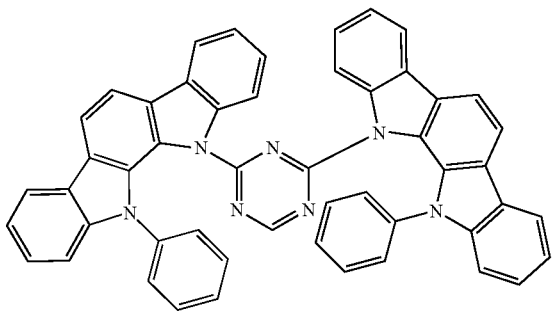
33
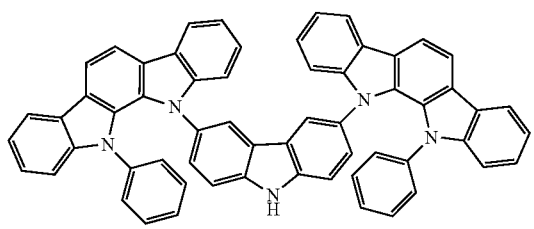
34
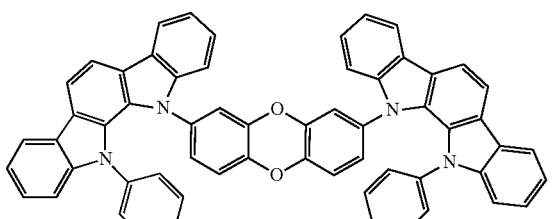

-continued
35
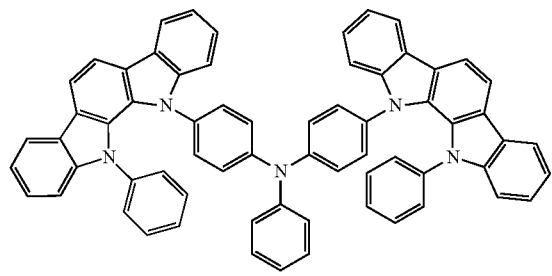
36
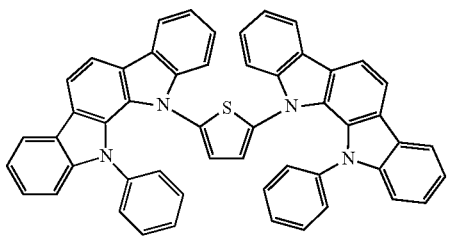
37
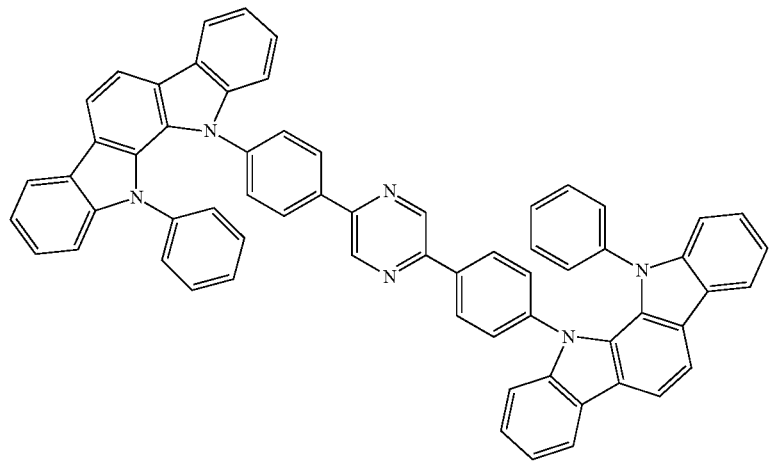
38
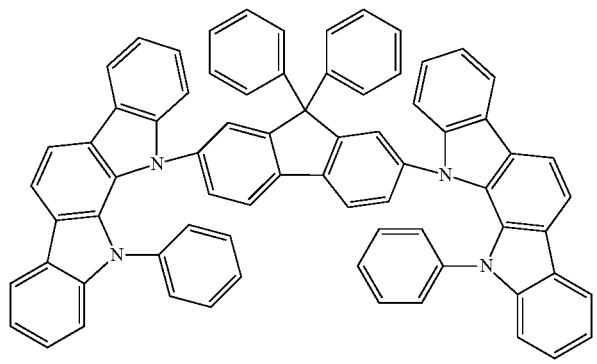
39
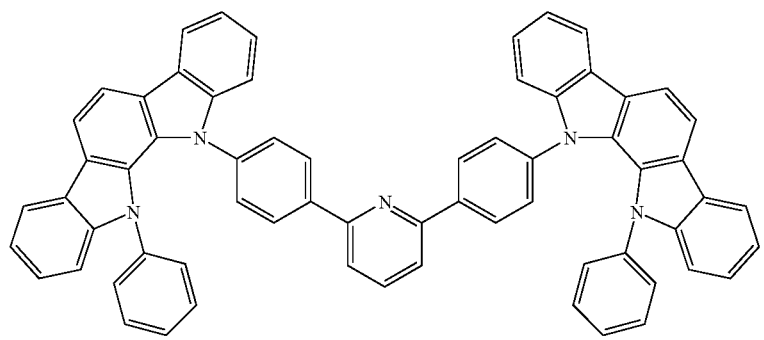

-continued
40
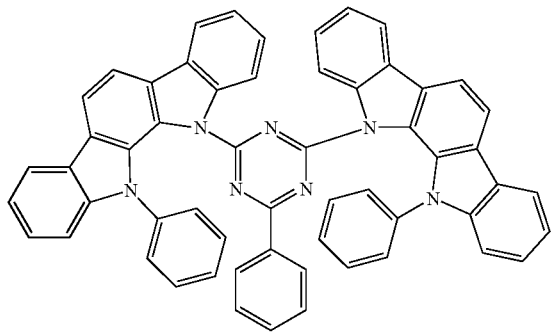
41
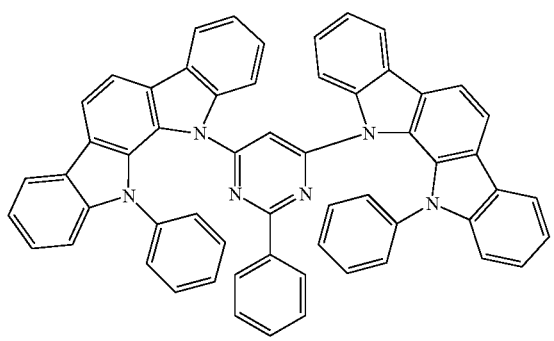
42
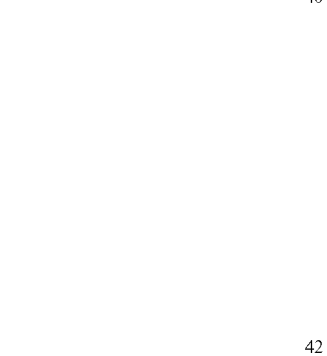
43
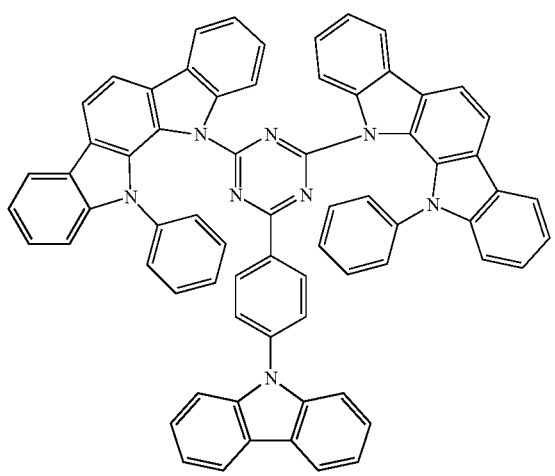
44
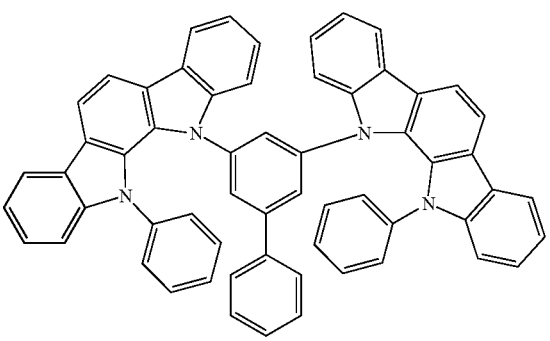
45
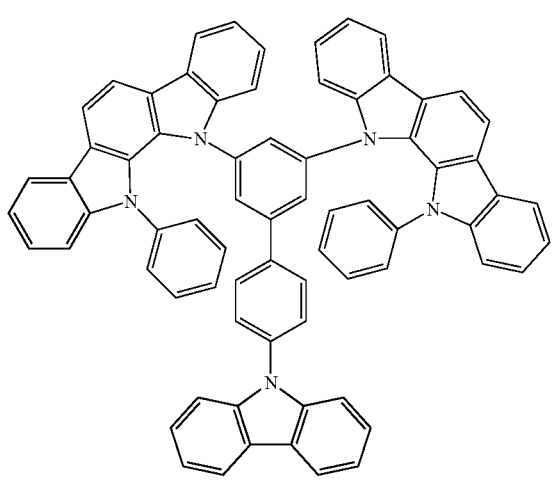
46
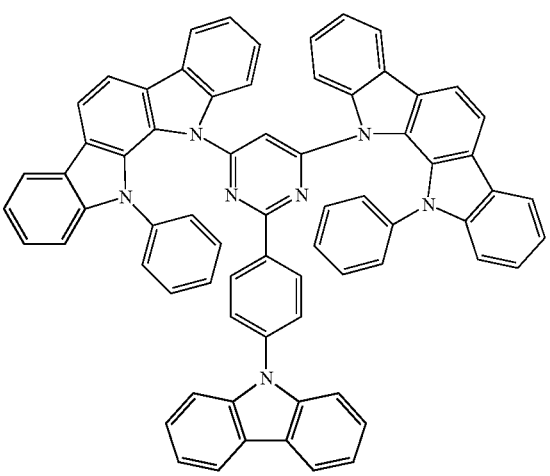

-continued
47
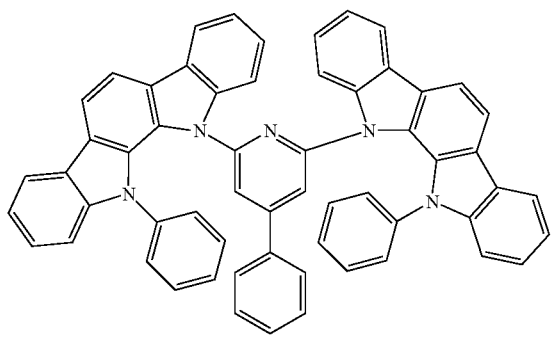
48
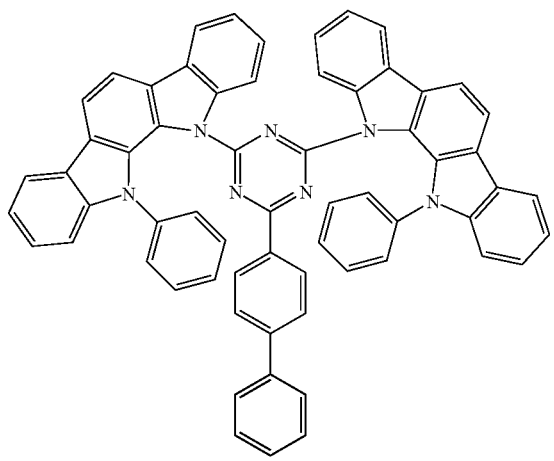
49
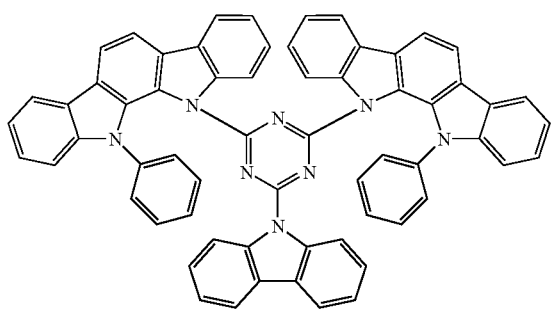
50
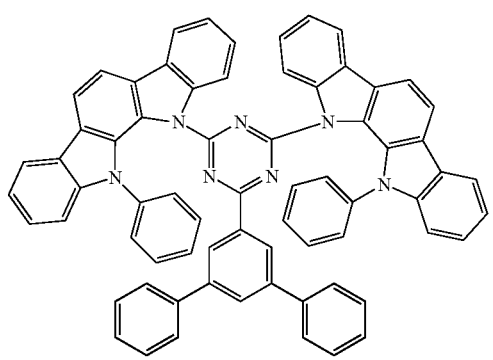
51
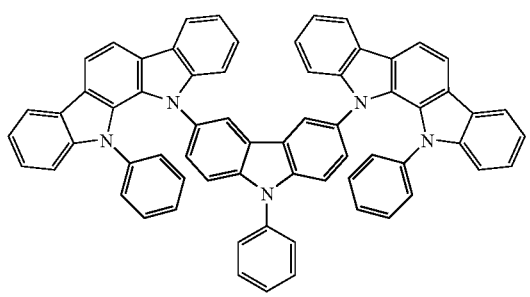
52
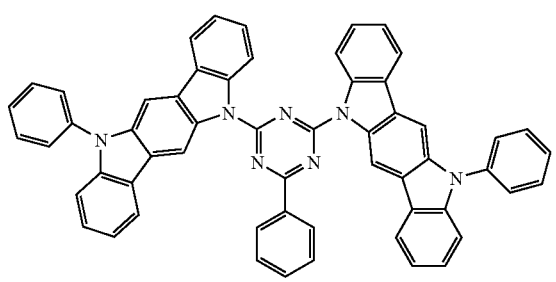
53
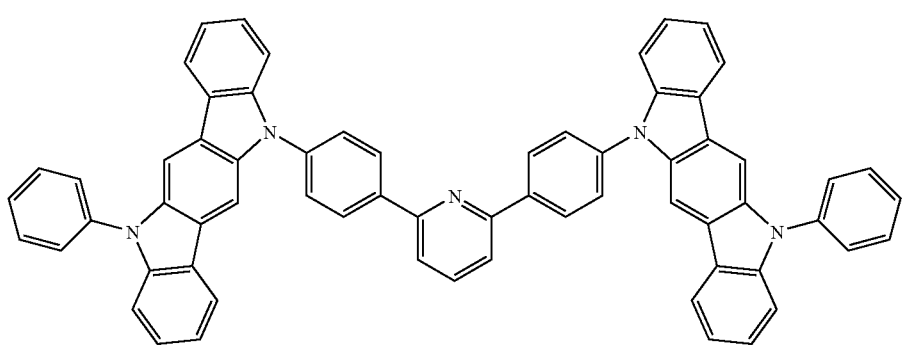

-continued
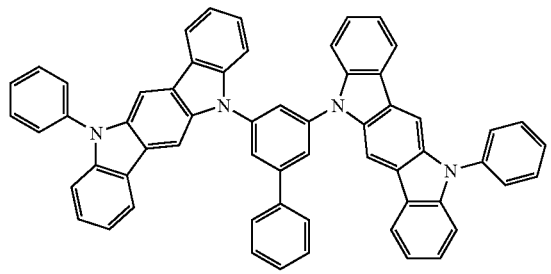
54
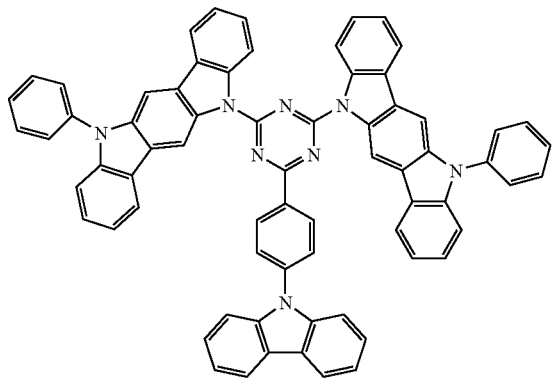
55
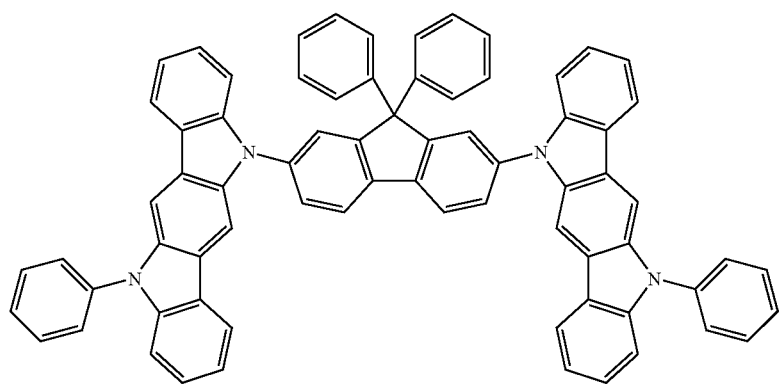
56
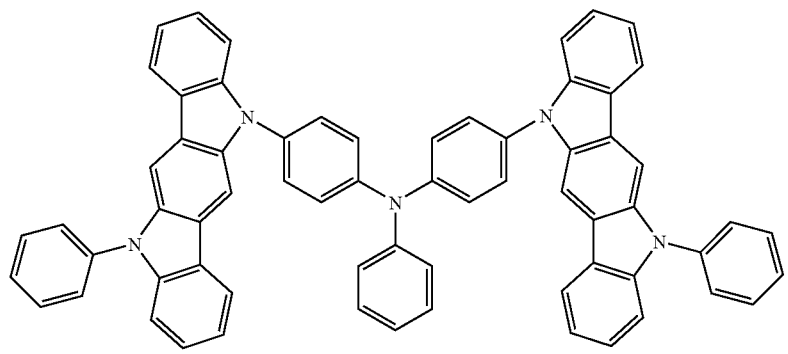
57
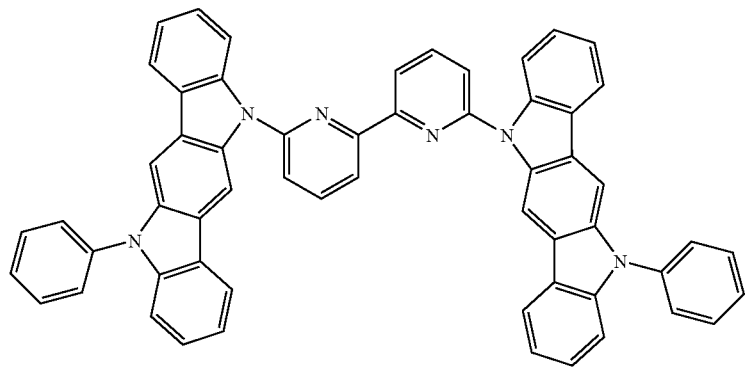
58

-continued
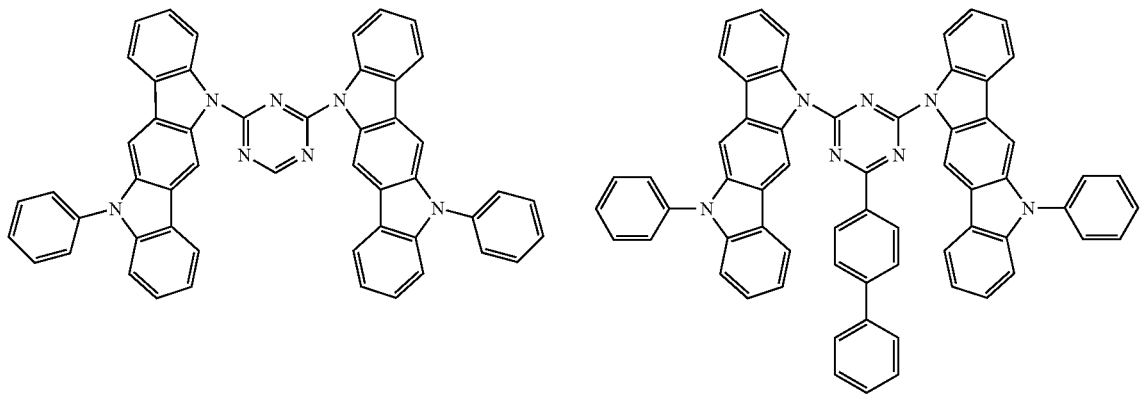
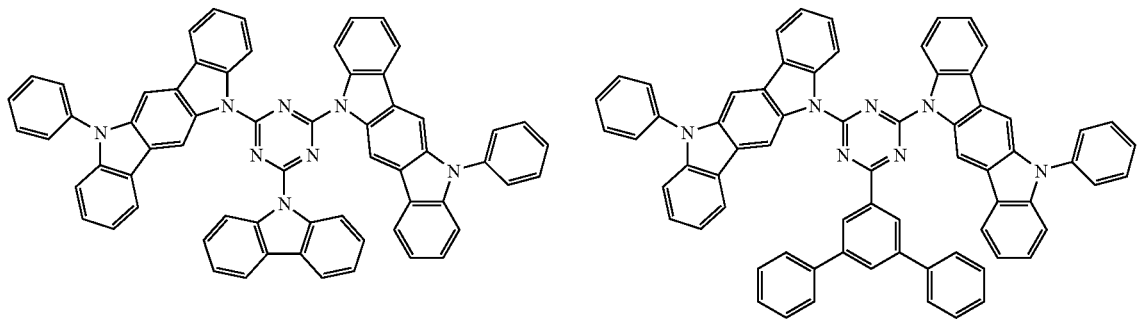
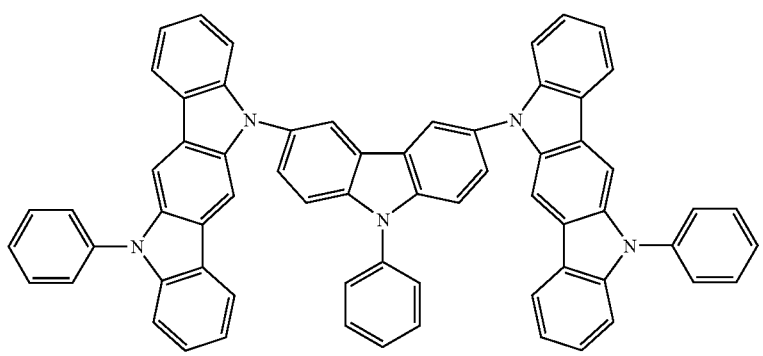

Preferable examples of the compounds for use in an organic EL device represented by the aforementioned general formula (1) wherein Y is represented by formula (1d) and n is 3 or greater are shown below, but are not limited thereto.
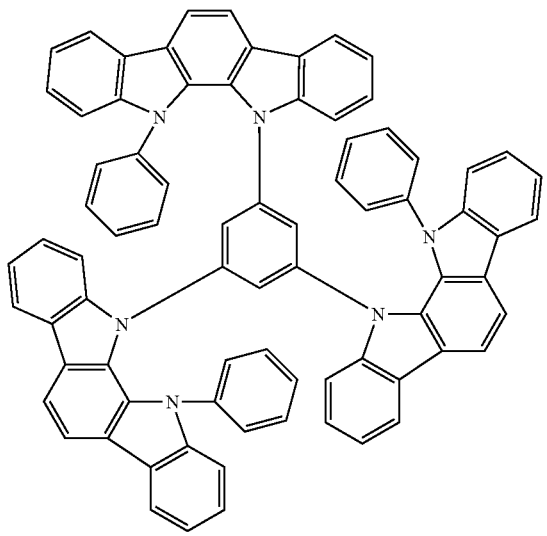
101
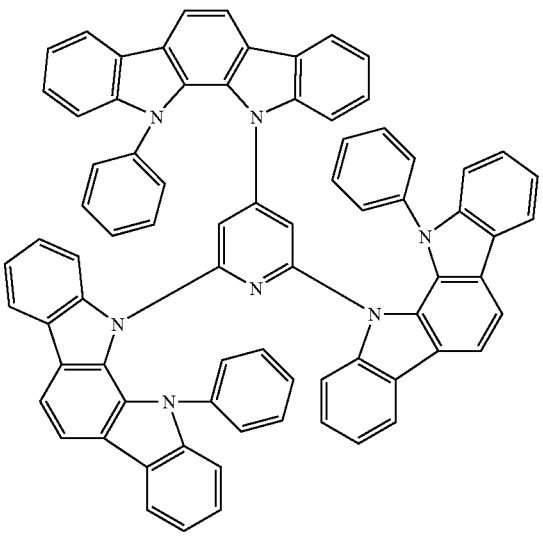
102
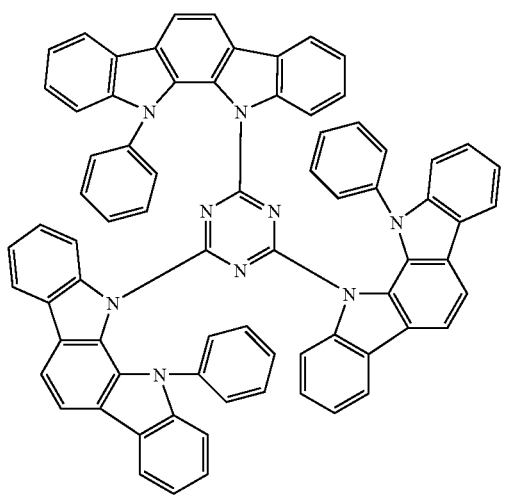
103
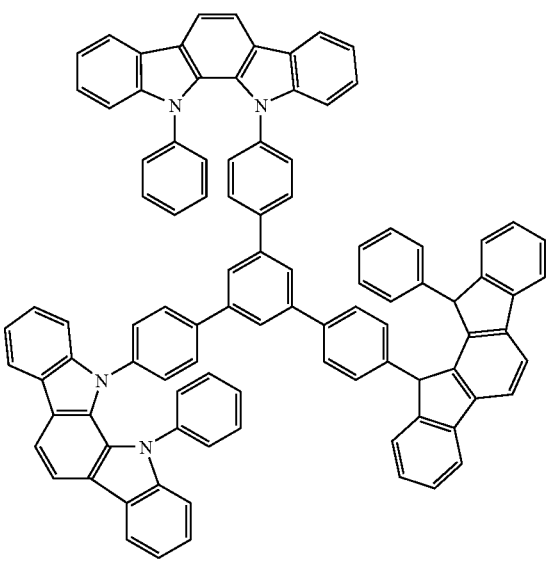
104

-continued
105
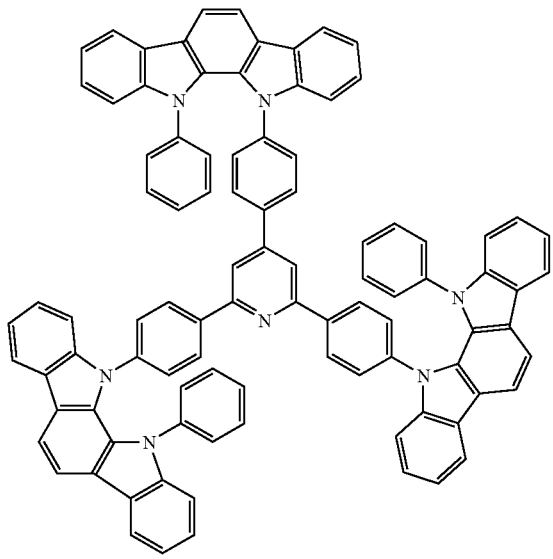
106
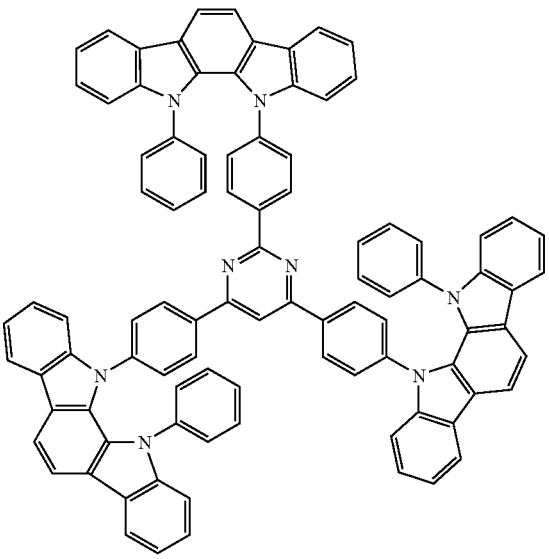
107
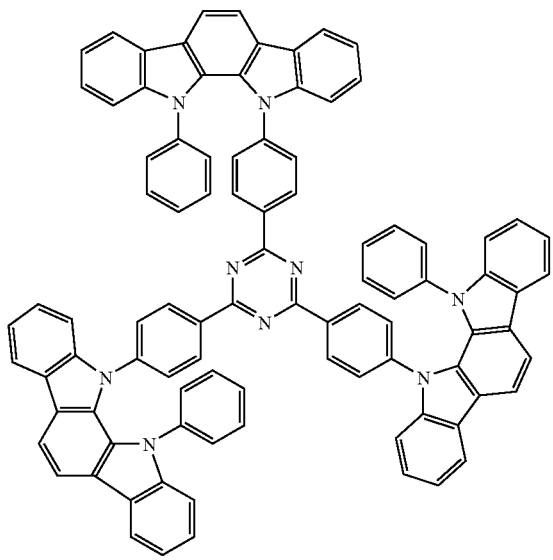
108
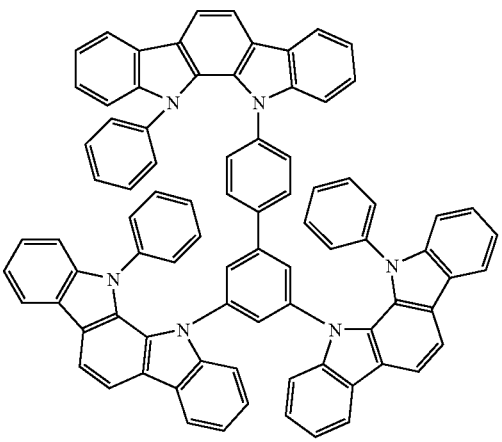
109
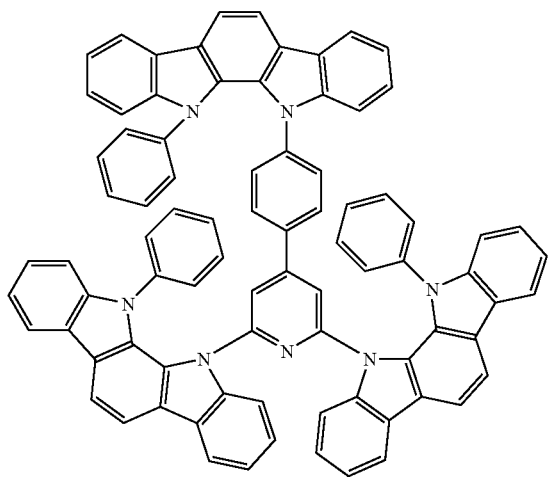
110
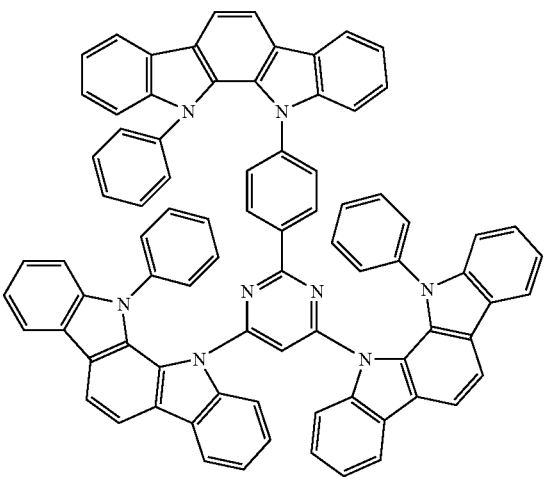

111
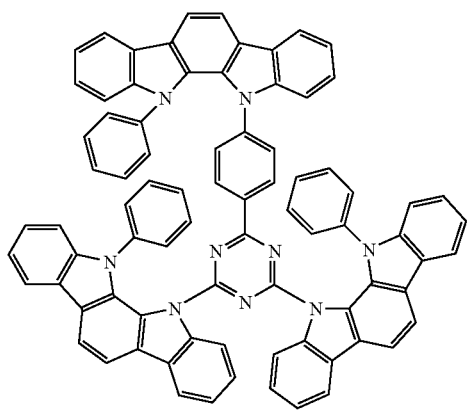
112
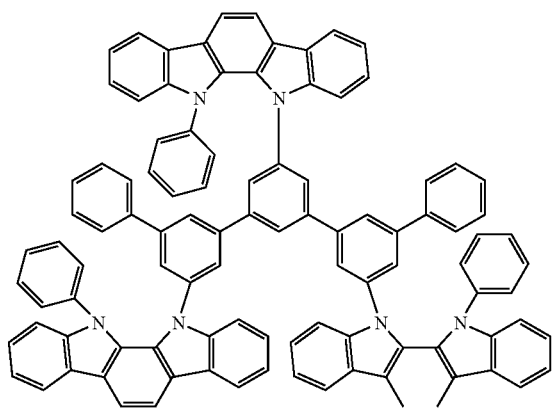
113
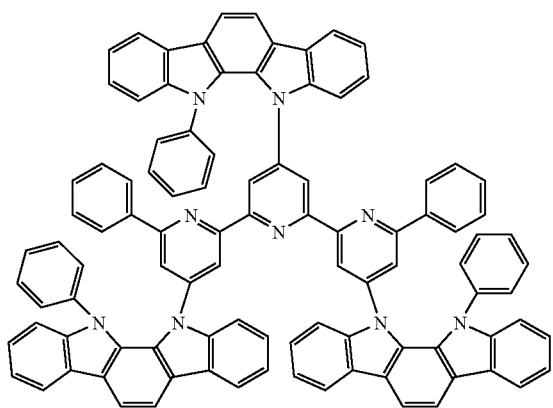
114
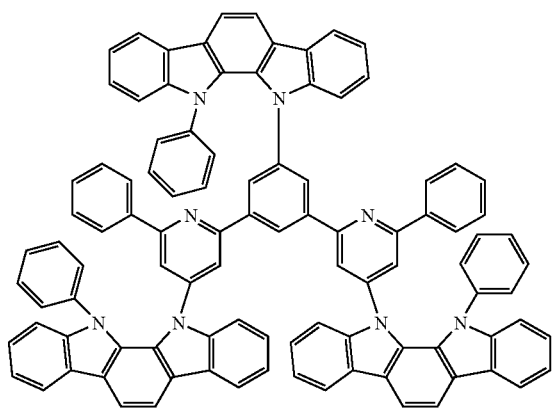
115
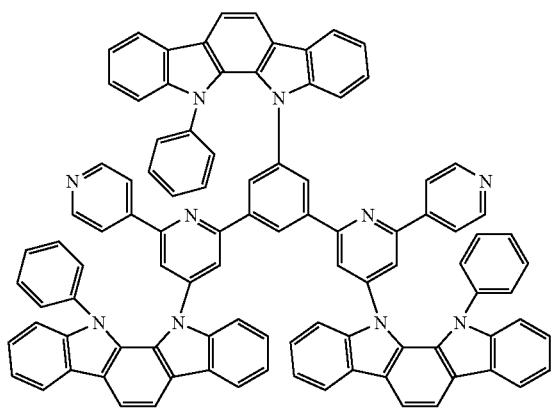
116
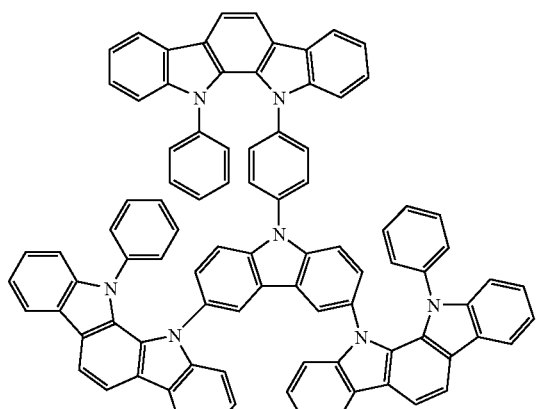

-continued
117
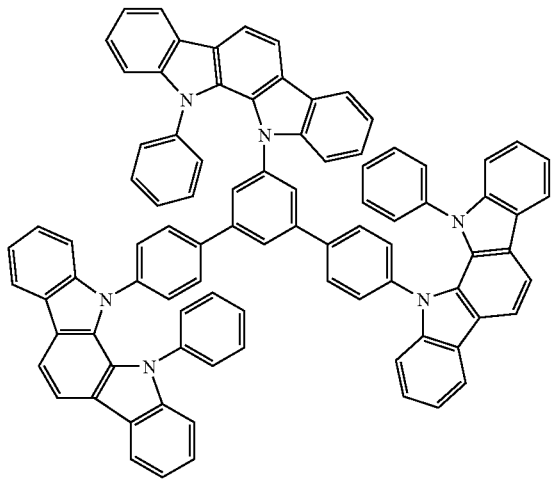
118
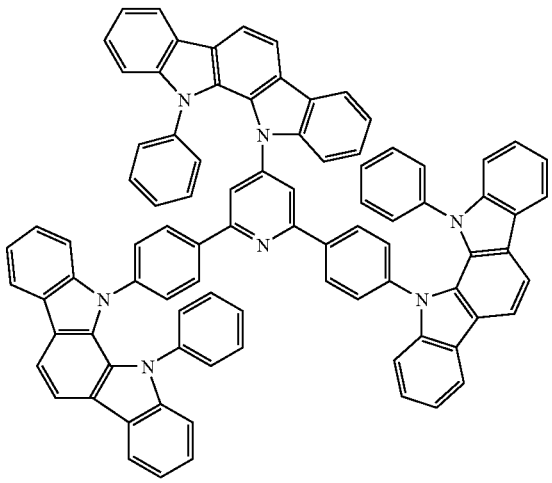
119
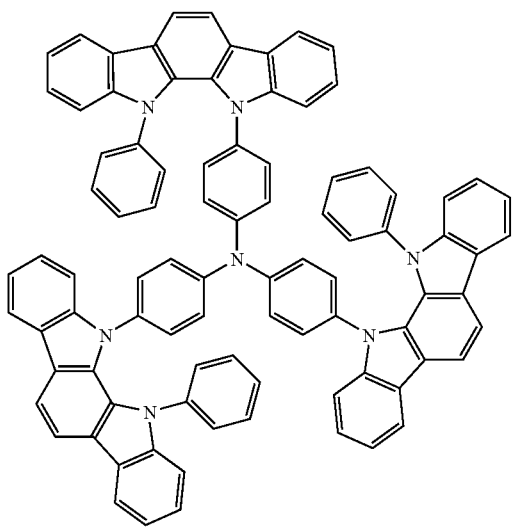
120
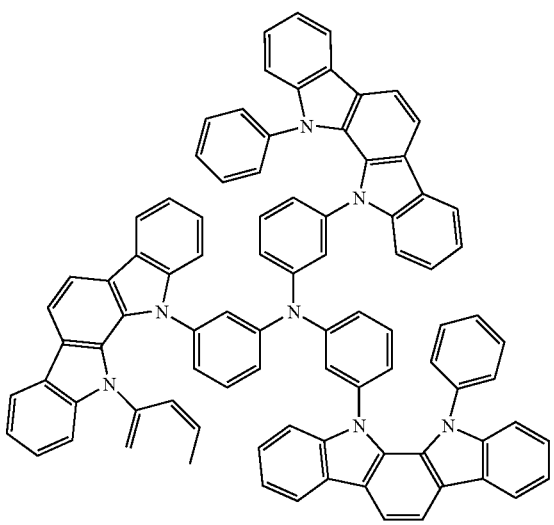
121
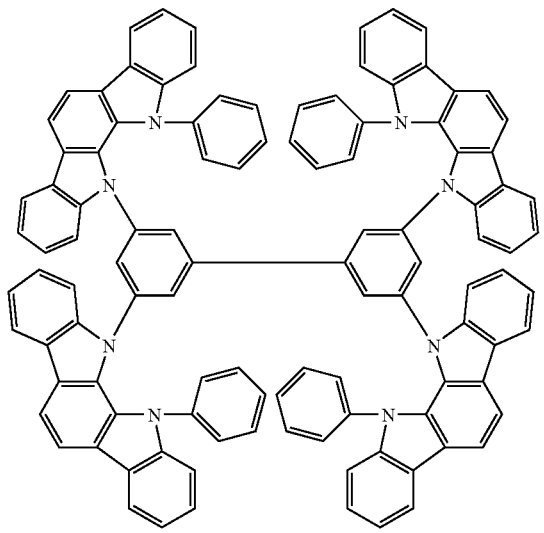
122
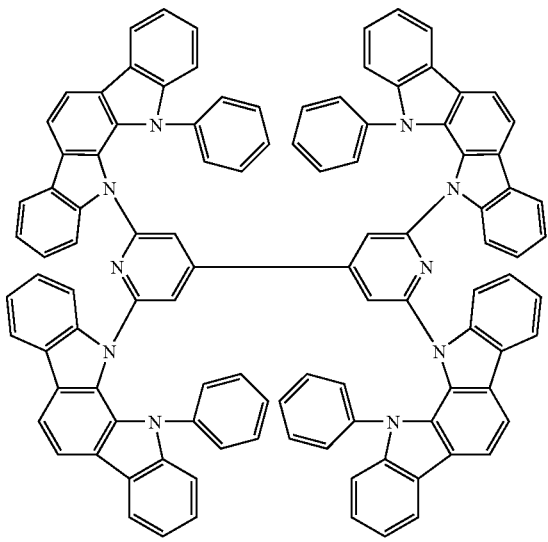

-continued
123
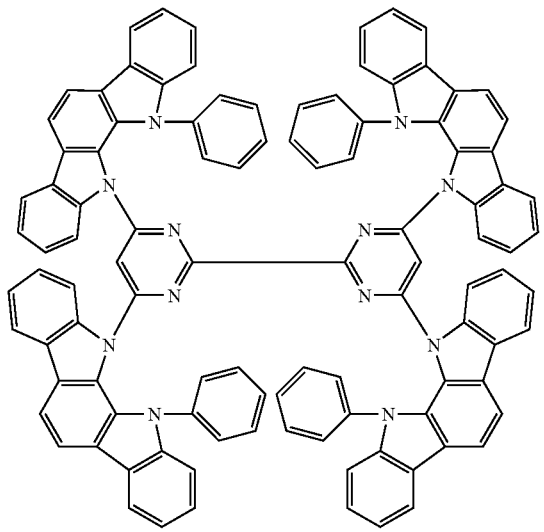
124
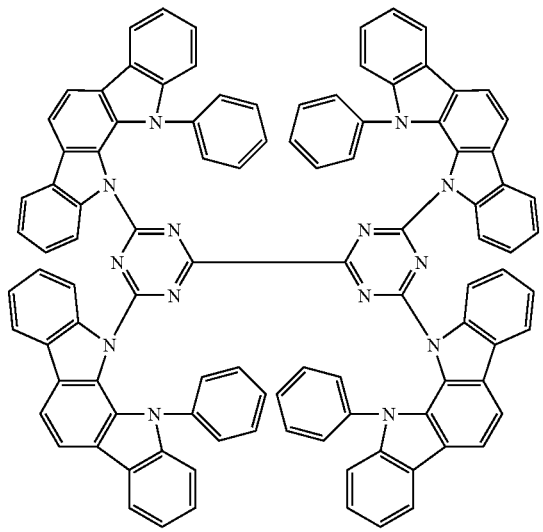
125
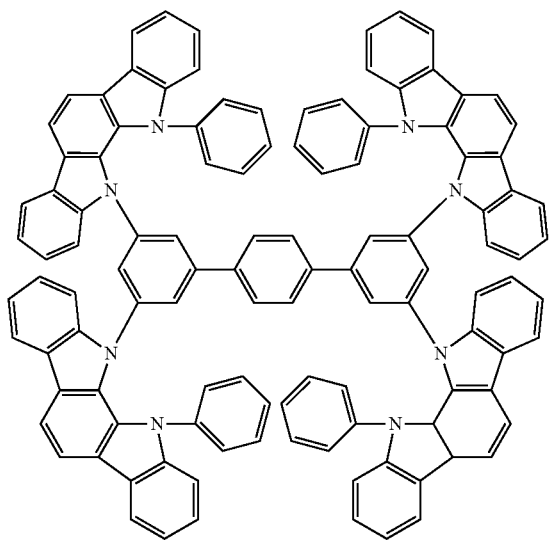
126
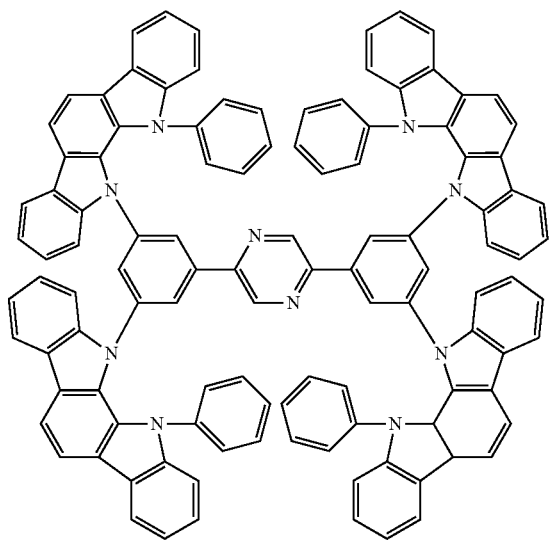
127
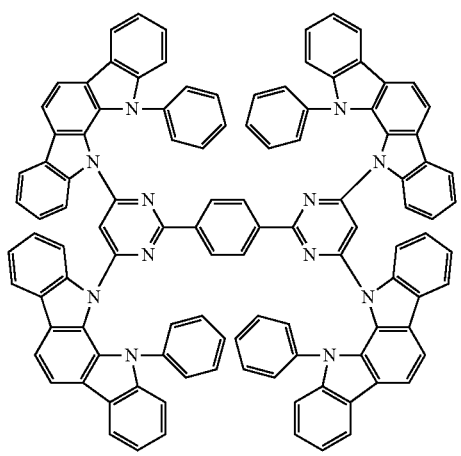
128
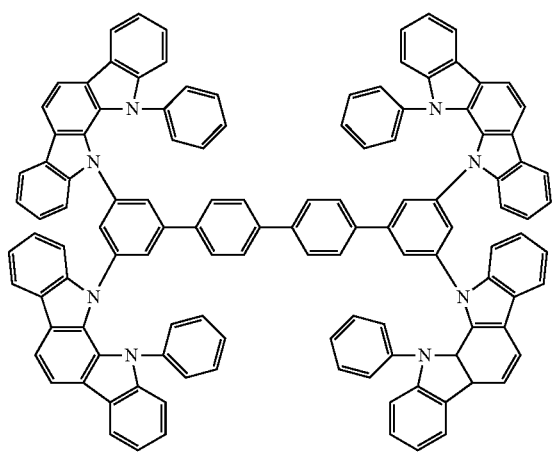

129
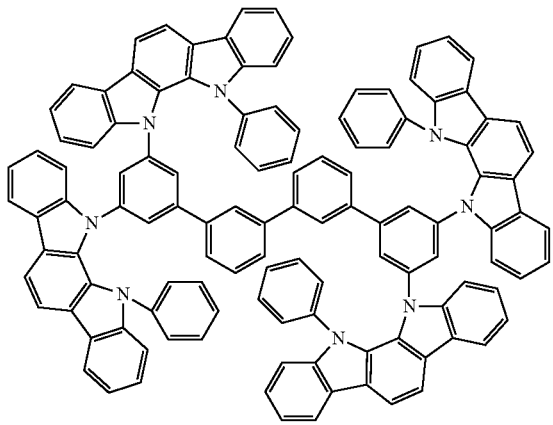
130
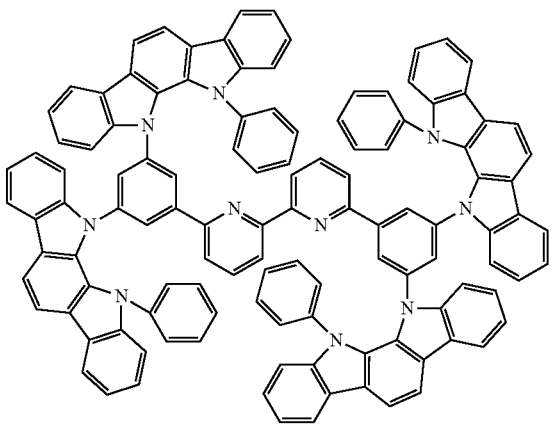
131
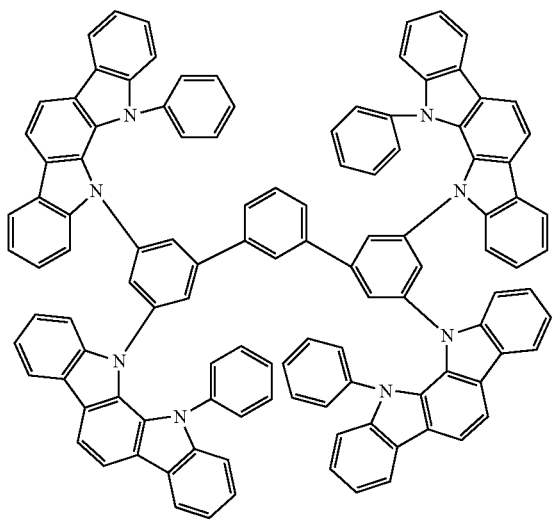
132
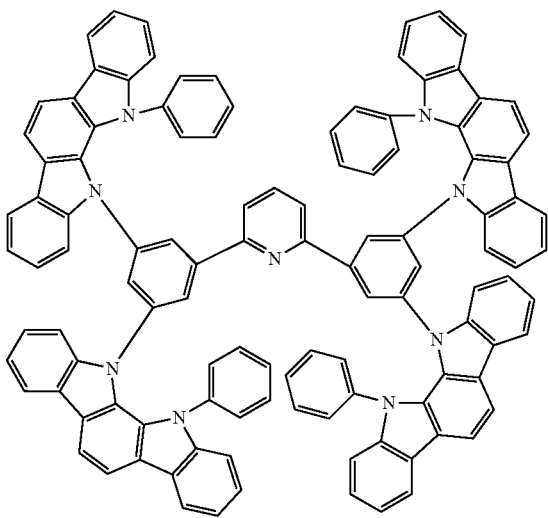
133
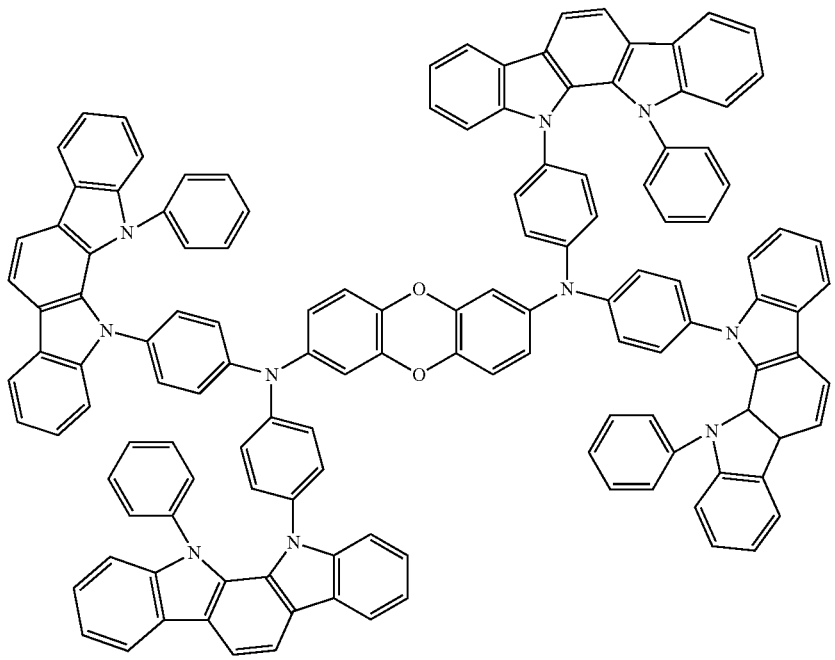

-continued
134
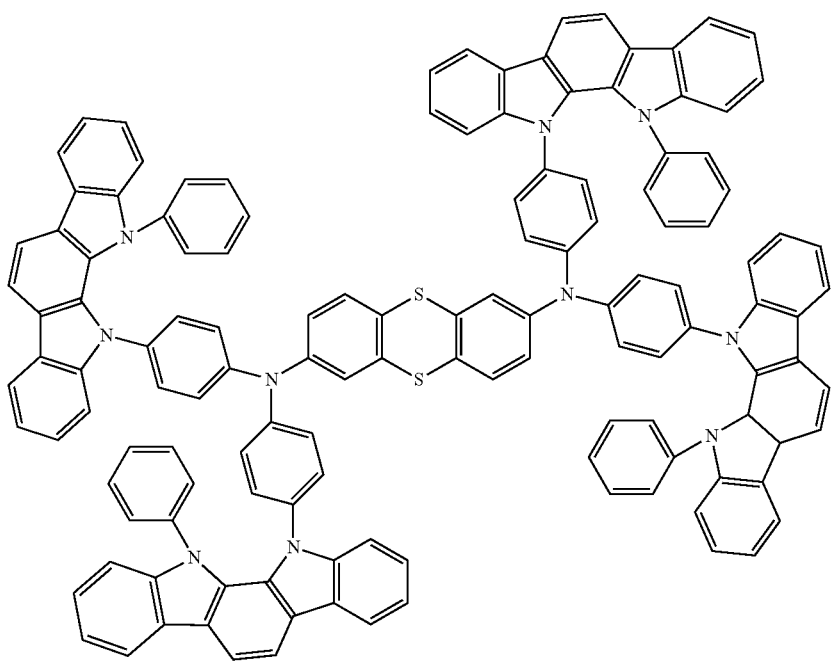
135
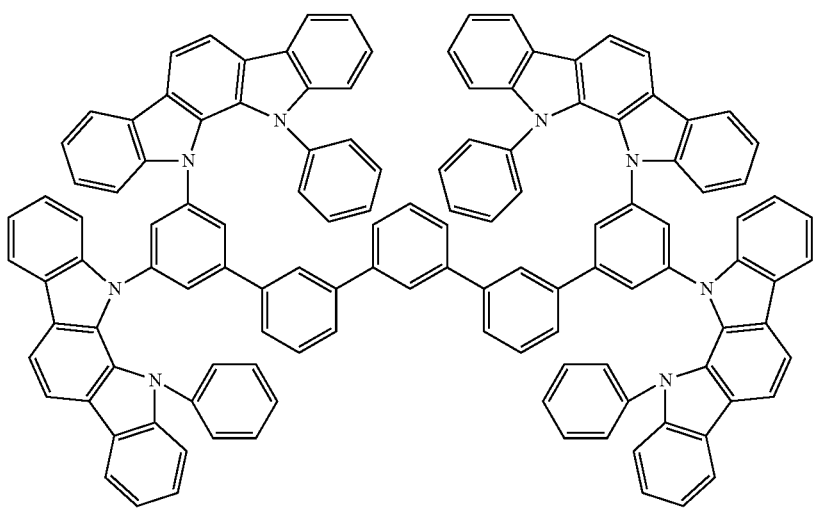
136
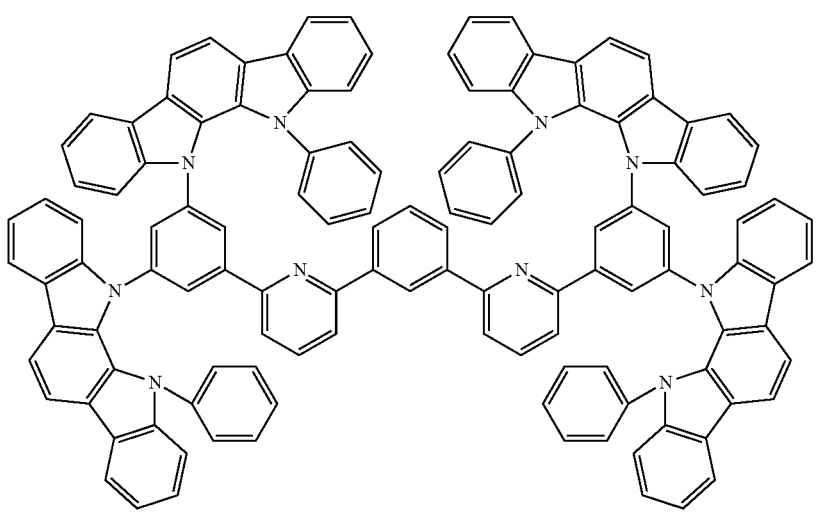

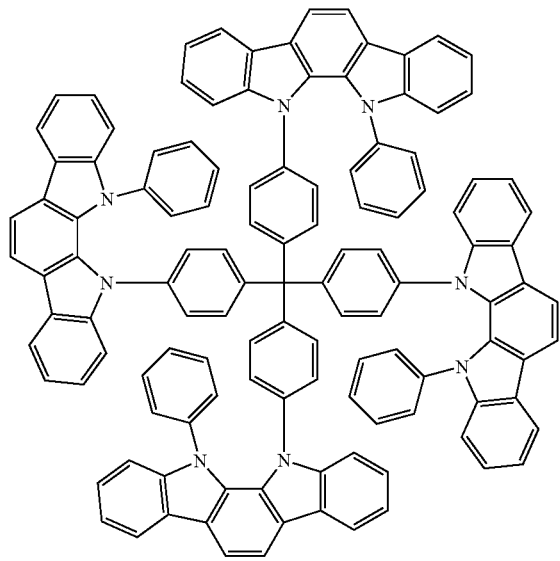

137

The organic EL device of this invention contains in its light-emitting layer a phosphorescent dopant and the aforementioned compound for use in an organic EL device as a host material. The materials useful for the phosphorescent dopants in the light-emitting layer include organic metal complexes containing at least one metal selected from ruthenium, rhodium, palladium, silver, rhenium, osmium, iridium, platinum, and gold. Such organic metal complexes are known in the aforementioned patent documents and any of them may be selected and used.

Preferable examples of the phosphorescent dopant include complexes containing a noble metal such as Ir in the center, typically Ir(ppy)3, complexes such as Ir(bt)2.acac3, and complexes such as PtOEt3. Concrete examples of these complexes are shown below, but are not limited thereto.

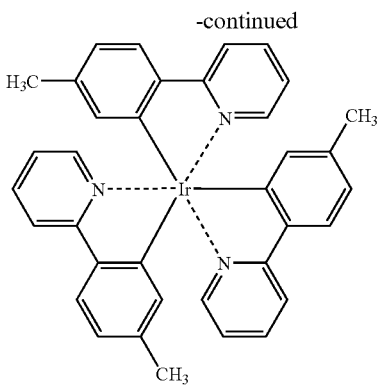

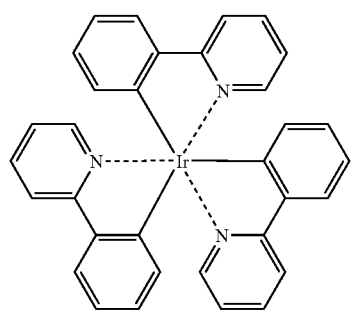

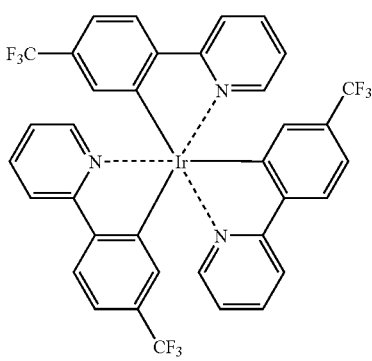

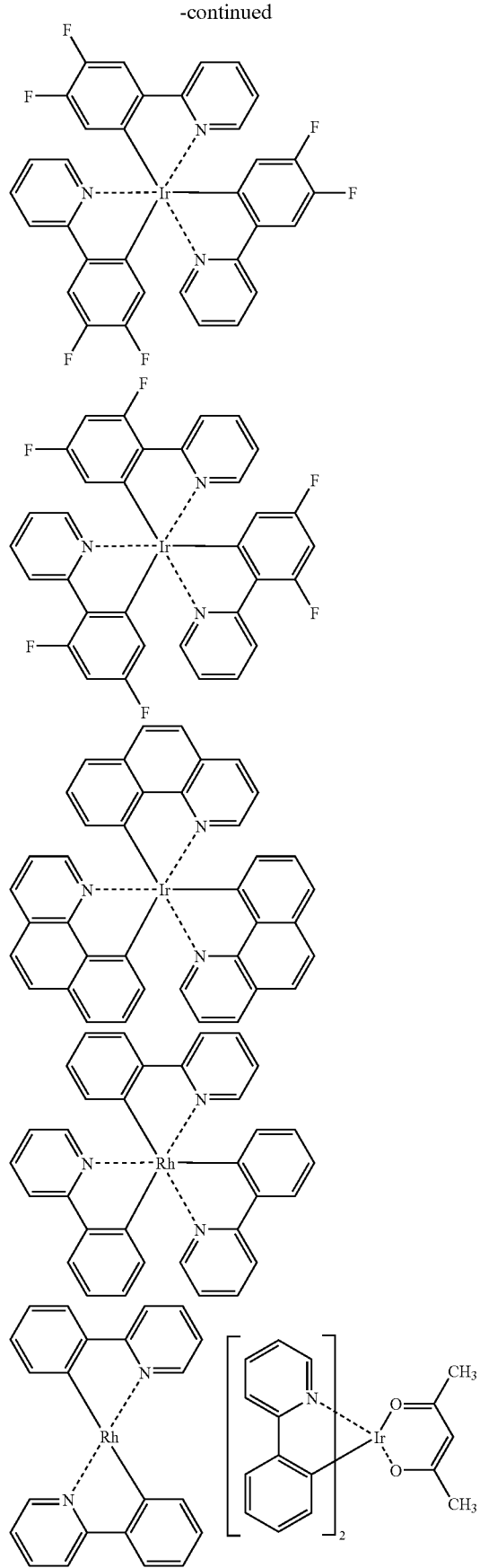
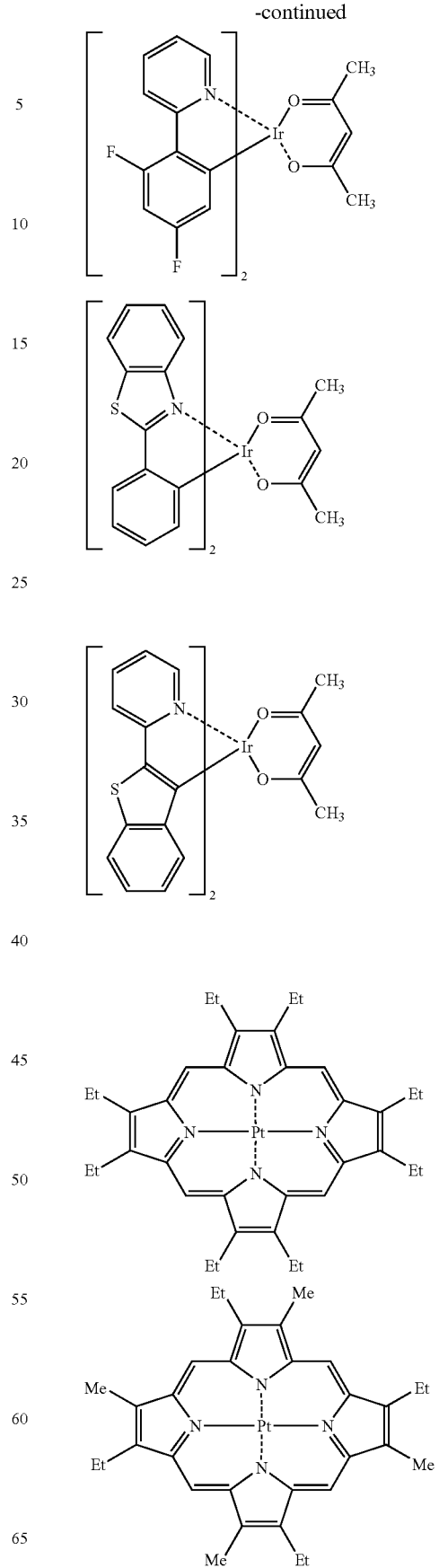

-continued

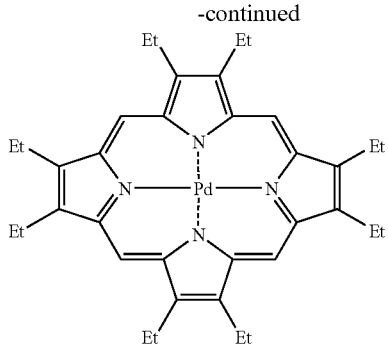

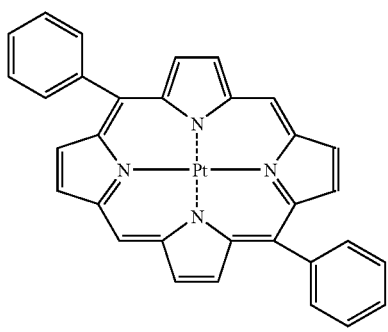

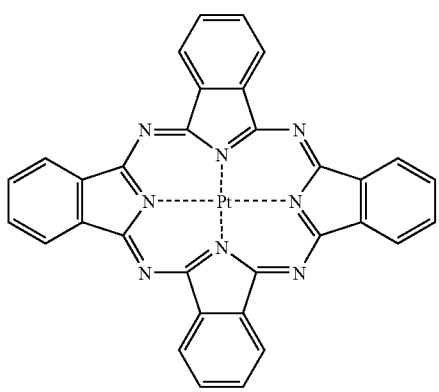

-continued

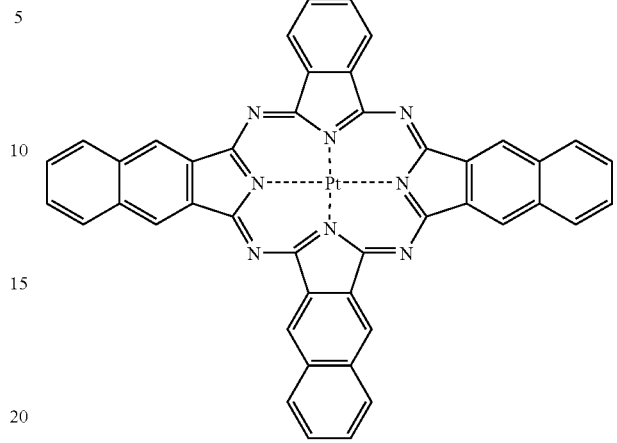

The content of the aforementioned phosphorescent dopant in the light-emitting layer is preferably in the range of 5 to 10 wt %.

The organic EL device of this invention comprises at least one light-emitting layer between an anode and a cathode piled one upon another on a substrate and the light-emitting layer contains a phosphorescent dopant and a compound represented by general formula (1).

EXPLANATION OF SYMBOLS

Figure 1:
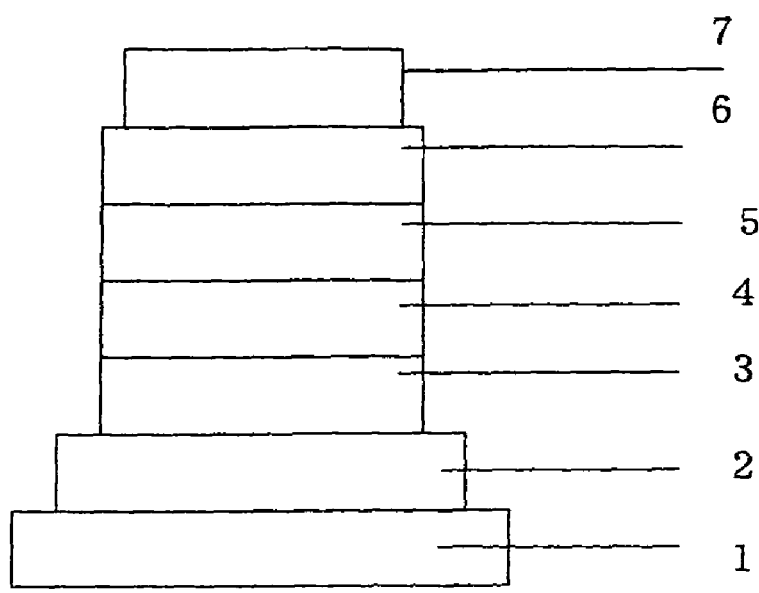
FIG. 1: A schematic drawing of an example of organic EL device.

1 Substrate, 2 Anode, 3 Hole-injecting layer, 4 Hole-transporting layer, 5 Light-emitting layer, 6 Electron-transporting layer, 7 Cathode.

PREFERRED EMBODIMENTS OF THE INVENTION

The structure of the organic EL device of this invention will be described below with reference to the drawing, but it will not be limited in any way to the illustrated structure.

FIG. 1 schematically shows the cross section of an example of organic EL device generally used in this invention. The numbers in FIG. 1 respectively designate the following; 1 substrate, 2 anode, 3 hole-injecting layer, 4 hole-transporting layer, 5 light-emitting layer, 6 electron-transporting layer, and 7 cathode. The organic EL device of this invention comprises the substrate, the anode, the light-emitting layer, and the cathode as essential layers and, in addition to the other non-essential layers, it advantageously has a hole-injecting/transporting layer and an electron-injecting/transporting layer and further has a hole-blocking layer disposed between the light-emitting layer and the electron-injecting/transporting layer. The hole-injecting/transporting layer means one or both of the hole-injecting layer and the hole-transporting layer while the electron-injecting/transporting layer means one or both of the electron-injecting layer and the electron-transporting layer.

It is possible to construct a device with a structure that is the reverse of the one shown in FIG. 1 by piling the cathode 7, the electron-transporting layer 6, the light-emitting layer 5, the hole-transporting layer 4, and the anode 2 one upon another in this order on the substrate 1 and, as described earlier, it is possible to dispose the organic EL device of this invention between two substrates at least one of which is highly transparent. In this case of the reverse structure, it is also possible to add or omit a layer or layers if necessary.

The organic EL device of this invention is applicable to a single device, a device with its structure arranged in array, or a device in which the anode and the cathode are arranged in X-Y matrix. The organic EL device of this invention produces remarkable improvement in luminous efficiency and driving stability over the conventional devices utilizing emission of light from the singlet state by incorporating a compound of specific skeleton and a phosphorescent dopant in its light-emitting layer and it can perform excellently when applied to full-color or multicolor panels.

EXAMPLES

This invention will be described in more detail below with reference to the examples, but it will not be limited to these examples and it can be executed in various modes. The compound number in the examples is the same as the one respectively assigned to the chemical formula shown earlier.

Example 1

Synthesis Of Compound 9

In a 200-ml three-necked flask that had been deaerated and filled with nitrogen were placed 5.0 g (44.59 mmol) of 1,2-cyclohexanedione and 12.9 g (89.21 mmol) of phenylhydrazine hydrochloride, then 145 ml of ethanol was added, and the mixture was stirred. To the contents of the flask was added 0.45 g (4.59 mmol) of concentrated sulfuric acid in drops over 5 minutes. The mixture was then heated to 65° C. and stirred at this temperature for 4 hours. The mixture was cooled to room temperature, the violet brown crystals formed were collected by filtration, reslurried twice with 50 ml of ethanol, and dried under reduced pressure to give 12.0 g (43.59 mmol, 97.7% yield) of a violet brown powder.

Then, 12.0 g (43.59 mmol) of the violet brown powder obtained above was placed in a 300-ml three-necked flask, 140 g of acetic acid and 8.0 g of trifluoroacetic acid were added, and the mixture was stirred. The mixture was then heated to 100° C. and stirred at this temperature for 15 hours. The mixture was cooled to room temperature, the yellow crystals formed were collected by filtration, rinsed with 200 ml of acetic acid, then rinsed with 200 ml of hexane, and dried under reduced pressure to give 5.0 g (19.51 mmol, 44.4% yield) of a white powder.

In a 200-ml three-necked flask that had been deaerated and filled with nitrogen were placed 4.0 g (15.61 mmol) of the white powder obtained above, 3.2 g (7.88 mmol) of 4,4'-diiodobiphenyl, 7.6 g (39.91 mmol) of copper iodide, 9.7 g (70.18 mmol) of potassium carbonate, and 150 ml of quinoline and stirred. The mixture was then heated to 190° C. and stirred at this temperature for 24 hours. The mixture was cooled to room temperature, 40.0 g (196.07 mmol) of iodobenzene and 7.6 g (39.91 mmol) of copper iodide were added, and the mixture was heated to 190° C. and stirred at this temperature for 3 days. The mixture was cooled to room temperature, 200 ml of water and 200 ml of dichloromethane were added, the mixture was stirred, and the yellow crystals formed were filtered. The filtrate was transferred to a 1000-ml separatory funnel and separated into the organic layer and the aqueous layer. The organic layer was washed three times with 200 ml of water, dehydrated over magnesium sulfate, the magnesium sulfate was filtered, the solvent was distilled off under reduced pressure, and the residue was purified by column chromatography to give 3.0 g (3.69 mmol, 46.8% yield) of a white powder (compound 9).

Compound 9 gave a molecular ion with a mass of 814 by EI-MS (M+1) and showed a melting point of 398° C.

Example 2

Synthesis of Compound 40

In a 2000-ml three-necked flask that had been deaerated and filled with nitrogen were placed 33.3 g (297.0 mmol) of 1,2-cyclohexanedione and 86.0 g (594.7 mmol) of phenylhydrazine hydrochloride, then 1000 ml of ethanol was added, and the mixture was stirred. To the contents of the flask was added 3.0 g (30.6 mmol) of concentrated sulfuric acid in drops over 5 minutes. The mixture was then heated to 65° C. and stirred at this temperature for 4 hours. The mixture was cooled to room temperature, the violet brown crystals formed were collected by filtration, reslurried twice with 500 ml of ethanol, and dried under reduced pressure to give 80.0 g (280.5 mmol, 96.3% yield) of a violet brown powder.

Then, 72.0 g (261.5 mmol) of the violet brown powder obtained above was placed in a 1000-ml three-necked flask, 720 g of acetic acid and 72.0 g of trifluoroacetic acid were added, and the mixture was stirred. The mixture was then heated to 100° C. and stirred at this temperature for 15 hours. The mixture was cooled to room temperature, the yellow crystals formed were collected by filtration, rinsed with 200 ml of acetic acid, then rinsed with 200 ml of hexane, and dried under reduced pressure to give 30.0 g (117.1 mmol, 44.8% yield) of a white powder.

In a 1000-ml three-necked flask that had been deaerated and filled with nitrogen were placed 26.0 g (101.4 mmol) of the white powder obtained above, 122.7 g (601.4 mmol) of iodobenzene, 54.7 g (287.2 mmol) of copper iodide, 66.7 g (482.6 mmol) of potassium carbonate, and 800 ml of quinoline and stirred. The mixture was then heated to 190° C. and stirred at this temperature for 72 hours. The mixture was cooled to room temperature, 500 ml of water and 500 ml of dichloromethane were added, the mixture was stirred, and the yellow crystals formed were filtered. The filtrate was transferred to a 2000-ml separatory funnel and separated into the organic layer and the aqueous layer. The organic layer was washed three times with 500 ml of water, dehydrated over magnesium sulfate, the magnesium sulfate was filtered, and the solvent was distilled off under reduced pressure. The residue was purified by column chromatography to give 13.7 g (41.2 mmol, 40.6% yield) of a white powder.

Thereafter, 2.16 g (49.5 mmol) of 55% sodium hydride and 70 ml of dehydrated N,N'-dimethylformamide were placed in a 500-ml three-necked flask that had been deaerated and filled with nitrogen, and the mixture was stirred in a stream of nitrogen. A solution of 13.7 g (41.2 mmol) of the white powder obtained immediately above in 70 ml of N,N'-dimethylformamide was prepared and added to the contents of the flask in drops over 15 minutes. After completion of the dropwise addition, the stirring was continued for one hour. Then, 70 ml of dehydrated N,N'-dimethylformamide was added to 3.76 g (20.4 mmol) of cyanuric chloride and the resulting solution was added to the contents of the flask in drops over 15 minutes. After completion of the dropwise addition, the stirring was continued for 2 hours, 350 g of water was added, and the crystals separated were collected by filtration, reslurried twice with 300 g of water, then reslurried with 300 g of methanol, dried under reduced pressure, and purified by column chromatography to give 10.9 g (14.0 mmol, 70.0% yield) of a white powder.

Then, 10.0 g (12.9 mmol) of the white powder obtained immediately above, 2.0 g (16.4 mmol) of phenylboronic acid, 1.5 g (1.3 mmol) of tetrakis(triphenylphosphine)palladium (0), 50 ml of ethanol, and 100 ml of toluene were placed in a 300-ml three-necked flask and stirred. A solution of 6.5 g (47.0 mmol) of sodium carbonate in 50 ml of water was added to the contents of the flask and the mixture was heated to 85° C. and stirred at this temperature for 5 hours. The mixture was cooled to room temperature, 100 ml of water and 100 ml of toluene were added, the mixture was stirred, and the insoluble matters were filtered. The filtrate was transferred to a 1000-ml separatory funnel and separated into the organic layer and the aqueous layer. The organic layer was washed three times with 100 ml of water, then dehydrated over magnesium sulfate, the magnesium sulfate was filtered, and the solvent was distilled off under reduced pressure. The residue was purified by column chromatography to give 5.3 g (6.5 mmol, 50.2% yield) of a yellow solid.

Compound 40 gave a molecular ion with a mass of 818 by EI-MS (M+1) and its melting point was not detected.

Example 3

Synthesis of Compound 27

In a 2000-ml three-necked flask that had been deaerated and filled with nitrogen were placed 33.3 g (297.0 mmol) of 1,2-cyclohexanedione and 86.0 g (594.7 mmol) of phenylhydrazine hydrochloride, then 1000 ml of ethanol was added, and the mixture was stirred. To the contents of the flask was added 3.0 g (30.6 mmol) of concentrated sulfuric acid in drops over 5 minutes. The mixture was then heated to 65° C. and stirred at this temperature for 4 hours. The mixture was cooled to room temperature, the violet brown crystals formed were collected by filtration, reslurried twice with 500 ml of ethanol, and dried under reduced pressure to give 80.0 g (280.5 mmol, 96.3% yield) of a violet brown powder.

Then, 72.0 g (261.5 mmol) of the violet brown powder obtained above was placed in a 1000-ml three-necked flask, 720 g of acetic acid and 72.0 g of trifluoroacetic acid were added, and the mixture was stirred. The mixture was then heated to 100° C. and stirred at this temperature for 15 hours. The mixture was cooled to room temperature, the yellow crystals formed were collected by filtration, rinsed with 200 ml of acetic acid, then rinsed with 200 ml of hexane, and dried under reduced pressure to give 30.0 g (117.1 mmol, 44.8% yield) of a white powder.

Then, 26.0 g (101.4 mmol) of the white powder obtained above, 122.7 g (601.4 mmol) of iodobenzene, 54.7 g (287.2 mmol) of copper iodide, 66.7 g (482.6 mmol) of potassium carbonate, and 800 ml of quinoline were placed in a 1000-ml three-necked flask that had been deaerated and filled with nitrogen and stirred. The mixture was then heated to 190° C. and stirred at this temperature for 72 hours. The mixture was cooled to room temperature, 500 ml of water and 500 ml of dichloromethane were added, the mixture was stirred, and the yellow crystals formed were filtered. The filtrate was transferred to a 2000-ml separatory funnel and separated into the organic layer and the aqueous layer. The organic layer was washed three times with 500 ml of water, dehydrated over magnesium sulfate, the magnesium sulfate was filtered, and the solvent was distilled off under reduced pressure. The residue was purified by column chromatography to give 13.7 g (41.2 mmol, 40.6% yield) of a white powder.

Then, 13.7 g (41.2 mmol) of the white powder obtained immediately above, 6.4 g (20.4 mmol) of 6,6'-dibromo-2,2'-dipyridyl, 1.14 g (5.98 mmol) of copper iodide, 25.22 g (118.8 mmol) of tripotassium phosphate, and 200 ml of 1,4-dioxane were place in a 2000-ml three-necked flask that had been deaerated and filled with nitrogen and stirred. To this mixture was added 10 ml of tranc-1,2-cyclohexanediamine with stirring. The mixture was then heated to 115° C. and stirred at this temperature for 15 hours. The mixture was cooled to room temperature and the insoluble matters were filtered. The filtrate was distilled under reduced pressure, methanol was added, and the white solid separated was collected by filtration and purified by column chromatography to give 5.0 g (6.14 mmol, 30.0% yield) of a white solid.

Compound 27 gave a molecular ion with a mass of 816 by EI-MS (M+1) and showed a melting point of 362° C.

Example 4

Compound 9 was deposited on a glass substrate from an evaporation source at a rate of 1.0 Å/sec to a thickness of 50 nm by the vapor deposition process at a degree of vacuum of $4.0 \times 10^{-4}$ Pa. The thin film thus formed was evaluated by a fluorometer.

Then, compound 9 and Ir(ppy)3 were codeposited on a glass substrate from different evaporation sources at a rate of 1.0 Å/sec to a thickness of 50 nm by the vapor deposition process at a degree of vacuum of $4.0 \times 10^{-4}$ Pa while controlling the concentration of Ir(ppy)3 at 7.0%.

The thin film thus formed was evaluated by a fluorometer. The maximum absorption wavelength of compound 9 was used as the excitation wavelength and the light then emitted was observed and compared with the light emitted from the thin film of compound 9 alone. The results are shown in Table 1.

Example 5

Compound 40 was deposited on a glass substrate from an evaporation source at a rate of 1.0 Å/sec to a thickness of 50 nm by the vapor deposition process at a degree of vacuum of $4.0 \times 10^{-4}$ Pa. The thin film thus formed was evaluated by a fluorometer.

Then, compound 40 and Ir(ppy)3 were codeposited on a glass substrate from different evaporation sources at a rate of 1.0 Å/sec to a thickness of 50 nm by the vapor deposition process at a degree of vacuum of $4.0 \times 10^{-4}$ Pa while controlling the concentration of Ir(ppy)3 at 7.0%.

The thin film thus formed was evaluated by a fluorometer. The maximum absorption wavelength of compound 40 was used as the excitation wavelength and the light then emitted was observed and compared with the light emitted from the thin film of compound 40 alone. The results are shown in Table 1.

Example 6

Compound 27 was deposited on a glass substrate from an evaporation source at a rate of 1.0 Å/sec to a thickness of 50 nm by the vapor deposition process at a degree of vacuum of $4.0 \times 10^{-4}$ Pa. The thin film thus formed was evaluated by a fluorometer.

Then, compound 27 and Ir(ppy)3 were codeposited on a glass substrate from different evaporation sources at a rate of 1.0 Å/sec to a thickness of 50 nm by the vapor deposition process at a degree of vacuum of $4.0 \times 10^{-4}$ Pa while controlling the concentration of Ir(ppy)3 at 7.0%.

The thin film thus formed was evaluated by a fluorometer. The maximum absorption wavelength of compound 27 was used as the excitation wavelength and the light then emitted was observed and compared with the light emitted from the thin film of compound 27 alone. The results are shown in Table 1.

Comparative Example 1

A thin film was formed as in Example 4 with the exception of changing the main component of the thin film to Alq3. The results are shown in Table 1. It is apparent from Table 1 that energy transition occurs to Ir(ppy)3 and emission of light from Ir(ppy)3 is observed when compound 9, compound 40, or compound 27 is used as the main component of the light-emitting layer; however, energy transition to Ir(ppy)3 does not occur and Alq3 itself emits fluorescent light when Alq3 is used as the main component.

TABLE 1

|  | Emission of light from host | Emission of light from dopant |
|---|---|---|
| Example 4 | X | ○ |
| Example 5 | X | ○ |
| Example 6 | X | ○ |
| Comparative example 1 | ○ | X |

Example 7

An organic EL device was constructed as in FIG. 1 with omission of a hole-injecting layer and addition of an electron-injecting layer. Applying the vacuum deposition process at a degree of vacuum of $4.0 \times 10^{-4}$ Pa, constituent layers in thin film were piled one upon another on a glass substrate on which a 150 nm-thick film of ITO had been formed as an anode. First, NPB was deposited on the ITO film to a thickness of 60 nm to form a hole-transporting layer.

Next, compound 9 and Ir(ppy)$_3$ were codeposited from different evaporation sources on the hole-transporting layer to a thickness of 25 nm to form a light-emitting layer. The concentration of Ir(ppy)$_3$ at this time was 7.0%. Then, Alq3 was deposited to a thickness of 50 nm to form an electron-transporting layer. Further, lithium fluoride (LiF) was deposited on the electron-transporting layer to a thickness of 0.5 nm to form an electron-injecting layer. Finally, aluminum (Al) as an electrode was deposited on the electron-injecting layer to a thickness of 170 nm to complete an organic EL device.

Example 8

An organic EL device was constructed as in FIG. 1 with omission of a hole-injecting layer and addition of an electron-injecting layer. Applying the vacuum deposition process at a degree of vacuum of $4.0 \times 10^{-4}$ Pa, constituent layers in thin film were piled one upon another on a glass substrate on which a 150 nm-thick film of ITO had been formed as an anode. First, NPB was deposited on the ITO film to a thickness of 60 nm to form a hole-transporting layer.

Next, compound 40 and Ir(ppy)$_3$ were codeposited from different evaporation sources on the hole-transporting layer to a thickness of 25 nm to form a light-emitting layer. The concentration of Ir(ppy)$_3$ at this time was 7.0%. Then, Alq3 was deposited to a thickness of 50 nm to form an electron-transporting layer. Further, lithium fluoride (LiF) was deposited on the electron-transporting layer to a thickness of 0.5 nm to form an electron-injecting layer. Finally, aluminum (Al) as an electrode was deposited on the electron-injecting layer to a thickness of 170 nm to complete an organic EL device.

Example 9

An organic EL device was constructed as in FIG. 1 with omission of a hole-injecting layer and addition of an electron-injecting layer. Applying the vacuum deposition process at a degree of vacuum of $4.0 \times 10^{-4}$ Pa, constituent layers in thin film were piled one upon another on a glass substrate on which a 150 nm-thick film of ITO had been formed as an anode. First, NPB was deposited on the ITO film to a thickness of 60 nm to form a hole-transporting layer.

Next, compound 27 and Ir(ppy)$_3$ were codeposited from different evaporation sources on the hole-transporting layer to a thickness of 25 nm to form a light-emitting layer. The concentration of Ir(ppy)$_3$ at this time was 7.0%. Then, Alq3 was deposited to a thickness of 50 nm to form an electron-transporting layer. Further, lithium fluoride (LiF) was deposited on the electron-transporting layer to a thickness of 0.5 nm to form an electron-injecting layer. Finally, aluminum (Al) as an electrode was deposited on the electron-injecting layer to a thickness of 170 nm to complete an organic EL device.

Each of the organic EL devices thus obtained was connected to an outside power source and, upon application of direct current voltage, emission of light with the characteristics shown in Table 2 was confirmed. The luminance, voltage, and luminous efficiency are measured at 10 mA./cm$^2$. The maximum wavelength of the spectrum of light emitted from the device is 517 nm and this proves that light is emitted from Ir(ppy)$_3$.

Comparative Example 2

An organic EL device was constructed as in Example 7 with the exception of using HMTPD in the hole-transporting layer and TAZ as the main component of the light-emitting layer.

Comparative Example 3

An organic EL device was constructed as in Example 7 with the exception of using TAZ as the main component of the light-emitting layer.

TABLE 2

|  | Luminance (cd/m$^2$) | Voltage (V) | Luminous efficiency (lm/W) |
|---|---|---|---|
| Example 7 | 2410 | 8.0 | 9.5 |
| Example 8 | 2300 | 6.0 | 12.0 |
| Example 9 | 2250 | 6.0 | 11.8 |
| Comparative example 2 | 2050 | 13.2 | 4.9 |
| Comparative example 3 | 1270 | 9.5 | 4.2 |

Example 10

Synthesis of Compound 103

In a 200-ml three-necked flask that had been deaerated and filled with nitrogen were placed 33.3 g (0.297 mole) of 1,2- cyclohexanedione and 86.0 g (0.595 mole) of phenylhydrazine hydrochloride, then 1000 ml of ethanol was added, and the mixture was stirred. To the contents of the flask was added 3.0 g (0.03 mole) of concentrated sulfuric acid in drops over 5 minutes. The mixture was then heated to 65° C. and stirred at this temperature for 4 hours. The mixture was cooled to room temperature, the violet brown crystals formed were collected by filtration, reslurried twice with 500 ml of ethanol, and dried under reduced pressure to give 80.0 g (0.286 mole, 96.3% yield) of a violet brown powder.

Then, 720 g of acetic acid and 72.0 g of trifluoroacetic acid were added to 72.0 g (0.258 mole) of the violet brown powder obtained above and stirred. The mixture was then heated to 100° C. and stirred at this temperature for 15 hours. The mixture was cooled to room temperature, the yellow crystals formed were collected by filtration, rinsed with 200 ml of acetic acid, then rinsed with 200 ml of hexane, and dried under reduced pressure to give 30.0 g (0.117 mole, 45.3% yield) of a white powder.

Then, 26.0 g (0.101 mole) of the white powder obtained above, 122.7 g (0.601 mole) of iodobenzene, 54.7 g (0.287 mole) of copper iodide, 66.7 g (0.482 mole) of potassium carbonate, and 800 ml of quinoline were placed in a 1000-ml three-necked flask that had been deaerated and filled with nitrogen and stirred. The mixture was then heated to 190° C. and stirred at this temperature for 72 hours. The mixture was cooled to room temperature, 500 ml of water and 500 ml of dichloromethane were added, the mixture was stirred, and the yellow crystals formed were filtered. The filtrate was transferred to a 2000-ml separatory funnel and separated into the organic layer and the aqueous layer. The organic layer was washed three times with 500 ml of water, dehydrated over magnesium sulfate, the magnesium sulfate was filtered, and the solvent was distilled off under reduced pressure. The residue was purified by column chromatography to give 13.7 g (0.04 mole, 40.8% yield) of a white powder.

Next, 2.16 g (49.5 mmol) of 55% sodium hydride and 70 ml of dehydrated N,N'-dimethylformamide were placed in a 500-ml three-necked flask that had been deaerated and filled with nitrogen and stirred in a stream of nitrogen. A solution of 13.7 g (40 mmol) of the white powder obtained immediately above in 70 ml of dehydrated N,N'-dimethylformamide was prepared and added to the contents of the flask in drops over 15 minutes. After completion of the dropwise addition, the stirring was continued for one hour. Thereafter, 2.46 g (13 mmol) of cyanuric chloride was dissolved in 70 ml of dehydrated N,N'-dimethylformamide and the resulting solution was added to the contents of the flask in drops over 15 minutes. After completion of the dropwise addition, the stirring was continued at an inside temperature of 80° C. for 24 hours, and the mixture was cooled to room temperature. Then, 350 g of water was added to the contents of the flask and the crystals separated were collected by filtration, reslurried twice with 300 g of water, then reslurried with 300 g of methanol, dried under reduced pressure, and purified by column chromatography to give 2.1 g (2.0 mmol, 15.5%) of a light yellow powder.

Compound 103 gave a molecular ion with a mass of 1072 by EI-MS (M+1) and showed a melting point of 492° C.

Example 11

Compound 103 was deposited on a glass substrate from an evaporation source at a rate of 1.0 Å/sec to a thickness of 50 nm by the vapor deposition process at a degree of vacuum of $4.0 \times 10^{-4}$ Pa. The thin film thus formed was evaluated by a fluorometer.

Then, compound 3 and Ir(ppy)3 were codeposited on a glass substrate from different evaporation sources at a rate of 1.0 Å/sec to a thickness of 50 nm by the vapor deposition process at a degree of vacuum of $4.0 \times 10^{-4}$ Pa while controlling the concentration of Ir(ppy)3 at 7.0%.

The thin film thus formed was evaluated by a fluorometer. The maximum absorption wavelength of compound 103 was used as the excitation wavelength and the light then emitted was observed and compared with the light emitted from the thin film of compound 103 alone. The results are shown in Table 3.

Comparative Example 4

A thin film was formed as in Example 11 with the exception of changing the maim component of the film to Alq3.

TABLE 3

|  | Emission of light from host | Emission of light from dopant |
|---|---|---|
| Example 11 | X | O |
| Comparative example 4 | O | X |

Example 12

An organic EL device was constructed as in FIG. 1 with omission of a hole-injecting layer and addition of an electron-injecting layer. Applying the vacuum deposition process at a degree of vacuum of $4.0 \times 10^{-4}$ Pa, constituent layers in thin film were piled one upon another on a glass substrate on which a 150 nm-thick film of ITO had been formed as an anode. First, NPB was deposited on the ITO film to a thickness of 60 nm to form a hole-transporting layer.

Next, compound 103 and Ir(ppy)$_3$ were codeposited from different evaporation sources on the hole-transporting layer to a thickness of 25 nm to form a light-emitting layer. The concentration of Ir(ppy)$_3$ at this time was 7.0%. Then, Alq3 was deposited to a thickness of 50 nm to form an electron-transporting layer. Further, lithium fluoride (LiF) was deposited on the electron-transporting layer to a thickness of 0.5 nm to form an electron-injecting layer. Finally, aluminum (Al) as an electrode was deposited on the electron-injecting layer to a thickness of 170 nm to complete an organic EL device.

The organic EL device thus obtained was connected to an outside power source and, upon application of direct current voltage, emission of light with the characteristics shown in Table 4 was confirmed. The luminance, voltage, and luminous efficiency are measured at 10 mA/cm$^2$. The maximum wavelength of the spectrum of light emitted from the device is 517 nm and this proves that light is emitted from Ir(ppy)$_3$.

Comparative Example 5

An organic EL device was constructed as in Example 12 with the exception of using HMTPD in the hole-transporting layer and TAZ as the main component of the light-emitting layer.

Comparative Example 6

An organic EL device was constructed as in Example 12 with the exception of using TAZ as the main component of the light-emitting layer.

TABLE 4

|  | Luminance (cd/m$^2$) | Voltage (V) | Luminous efficiency (lm/W) |
|---|---|---|---|
| Example 12 | 2100 | 6.7 | 9.8 |
| Comparative example 4 | 2050 | 13.2 | 4.9 |
| Comparative example 5 | 1270 | 9.5 | 4.2 |

INDUSTRIAL APPLICABILITY

The organic EL device of this invention can emit light of high luminance at high efficiency with application of low voltage. In consequence, the organic EL device is applicable to flat panel displays (for example, office computers and wall-hanging television sets), vehicle display devices, cellular phone displays, light sources utilizing the characteristics of planar light emitters (for example, light sources of copiers and backlight sources of liquid crystal displays and instruments), signboards, and beacon lights and has a high technical value.

What is claimed is:

1. A compound for use in an organic electroluminescent device represented by the following general formula (1):

$$Z\text{-}(Y)_n \quad (1)$$

wherein, Z is a linking group consisting of a substituted or unsubstituted aromatic hydrocarbon group or a substituted or unsubstituted aromatic heterocyclic group, Y is a group represented by the following general formula (1a), and n is an integer of 2 or greater;

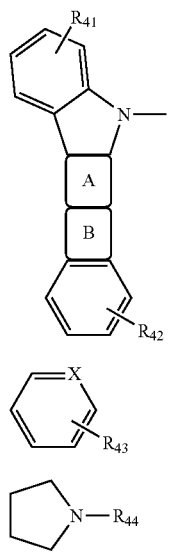

(1a)

(1b)

(1c)

wherein, ring A is an aromatic or heterocyclic ring condensed with the adjacent rings and represented by formula (1b), ring B is a heterocyclic ring condensed with the adjacent rings and represented by formula (1c), X is carbon or nitrogen, R$_{43}$ is hydrogen, a substituted or unsubstituted aromatic hydrocarbon group, a substituted or unsubstituted aromatic heterocyclic group, or a ring condensed with the X-containing ring, R$_{44}$ is a substituted or unsubstituted aromatic hydrocarbon group or a substituted or unsubstituted aromatic heterocyclic group, and each of R$_{41}$ and R$_{42}$ is hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, a substituted or unsubstituted aromatic hydrocarbon group, or a substituted or unsubstituted aromatic heterocyclic group.

2. A compound for use in an organic electroluminescent device as described in claim 1 wherein Y in general formula (1) is a group represented by general formula (1d):

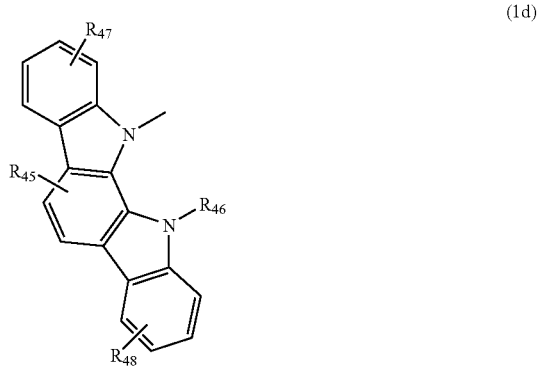

(1d)

wherein, R$_{45}$ has the same meaning as R$_{43}$, R$_{46}$ has the same meaning as R$_{44}$, and each of R$_{47}$ and R$_{48}$ independently has the same meaning as R$_{41}$.

3. A compound for use in an organic electroluminescent device as described in claim 1 wherein n is 3 or 4 in general formula (1).

4. An organic electroluminescent device comprising a light-emitting layer disposed between an anode and a cathode piled one upon another on a substrate wherein the light-emitting layer contains a phosphorescent dopant and the compound for use in an organic electroluminescent device described in claim 1 as a host material.

5. An organic electroluminescent device as described in claim 4 wherein a hole-injecting/transporting layer is disposed between the anode and the light-emitting layer and an electron-injecting/transporting layer is disposed between the cathode and the light-emitting layer.

6. An organic electroluminescent device as described in claim 5 wherein a hole-blocking layer is disposed between the light-emitting layer and the electron-injecting/transporting layer.

7. A compound for use in an organic electroluminescent device as described in claim 1 wherein the compound is represented by the following general formula (2) or (3):

(2)

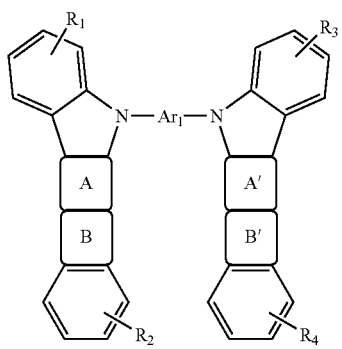

(2a)

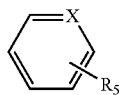

(2b)

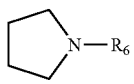

wherein, each of ring A and ring A' is an aromatic or heterocyclic ring condensed with the adjacent rings and represented by formula (2a), each of ring B and ring B' is a heterocyclic ring condensed with the adjacent rings and represented by formula (2b), $Ar_1$ is a divalent linking group consisting of a non-condensed substituted or unsubstituted aromatic hydrocarbon group or a non-condensed substituted or unsubstituted aromatic heterocyclic group, X is carbon or nitrogen, $R_5$ is a non-condensed substituted or unsubstituted aromatic hydrocarbon group or a non-condensed substituted or unsubstituted aromatic heterocyclic group, and each of $R_1$ to $R_4$ is independently hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, a substituted or unsubstituted aromatic hydrocarbon group, or a substituted or unsubstituted aromatic heterocyclic group;

(3)

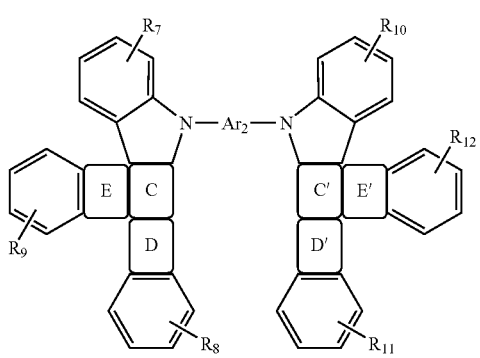

(3a)

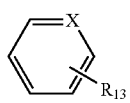

(3b)

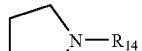

(3c)

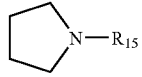

wherein, each of ring C and ring C' is an aromatic or heterocyclic ring condensed with the adjacent rings and represented by formula (3a), each of ring D and ring D' is a heterocyclic ring condensed with the adjacent rings and represented by formula (3b), each of ring E and ring E' is a heterocyclic ring condensed with the adjacent rings and represented by formula (3c), $Ar_2$ is a divalent linking group consisting of a non-condensed substituted or unsubstituted aromatic hydrocarbon group or a non-condensed substituted or unsubstituted aromatic heterocyclic group, X is carbon or nitrogen, $R_{13}$ has the same meaning as $R_5$, each of $R_{14}$ and $R_{15}$ independently has the same meaning as $R_6$, and each of $R_7$ to $R_{12}$ independently has the same meaning as $R_1$.

8. A compound for use in an organic electroluminescent device as described in claim 7 wherein each of ring A, ring A', ring C, and ring C' is a benzene ring, each of $R_6$, $R_{14}$, and $R_{15}$, is a substituted or unsubstituted phenyl or pyridyl group, and each of $R_1$ to $R_4$, and $R_7$ to $R_{12}$ is hydrogen or a phenyl group in general formulas (2) to (3) and formulas (2a), 2(b) and (3a) to (3c).

9. A compound for use in an organic electroluminescent device as described in claim 1 wherein the compound is represented by the following general formula (4) or (5):

(4)

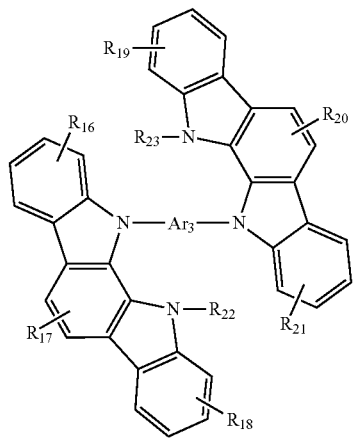

wherein, $Ar_3$ is a divalent linking group consisting of a non-condensed substituted or unsubstituted aromatic hydrocarbon group or a non-condensed substituted or unsubstituted aromatic heterocyclic group, each of $R_{17}$ and $R_{20}$ is hydrogen, a non-condensed substituted or unsubstituted aromatic hydrocarbon group, or a non-condensed substituted or unsubstituted aromatic heterocyclic group, each of $R_{22}$ and $R_{23}$ is a non-condensed substituted or unsubstituted aromatic hydrocarbon group or a non-condensed substituted or unsubstituted aromatic heterocyclic group, and each of $R_{16}$, $R_{18}$, $R_{19}$, and $R_{21}$ is hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, a substituted or unsubstituted aromatic hydrocarbon group, or a substituted or unsubstituted aromatic heterocyclic group;

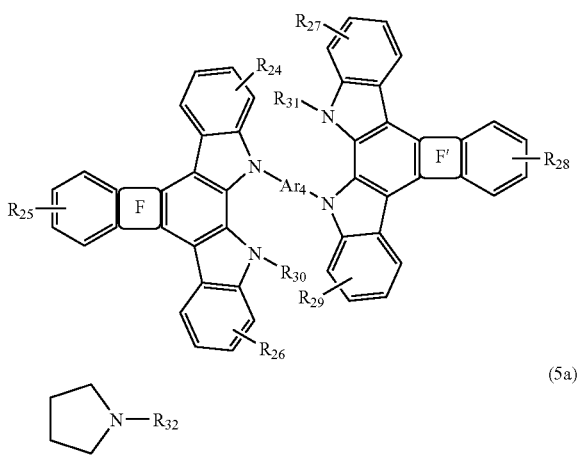

(5)

(5a)

wherein, each of ring F and ring F' is a heterocyclic ring condensed with the adjacent rings and represented by formula (5a), Ar$_4$ has the same meaning as Ar$_3$, each of R$_{30}$ to R$_{32}$ independently has the same meaning as R$_{22}$, and each of R$_{24}$ to R$_{29}$ independently has the same meaning as R$_{16}$.

10. A compound for use in an organic electroluminescent device as described in claim 9 wherein each of R$_{22}$, R$_{23}$, and R$_{30}$ to R$_{32}$ is a substituted or unsubstituted phenyl or pyridyl group, and each of R$_{16}$ to R$_{21}$, and R$_{24}$ to R$_{29}$ is hydrogen or a phenyl group in general formulas (4), (5) and formula (5a).

11. A compound for use in an organic electroluminescent device represented by the following general formula (1):

$$Z-(Y)_n \quad (1)$$

wherein, Z is a linking group consisting of a non-condensed substituted or unsubstituted aromatic hydrocarbon group or a non-condensed substituted or unsubstituted aromatic heterocyclic group, Y is a group represented by the following general formula (1a), and n is an integer of 2 or greater;

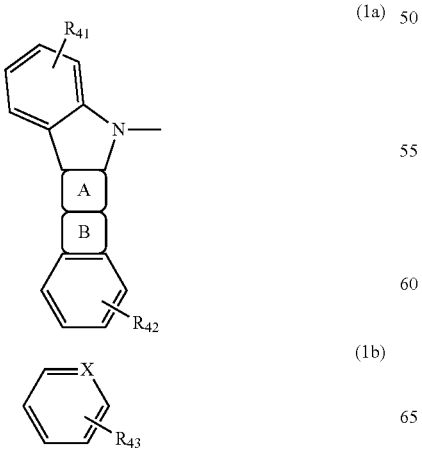

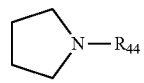

(1c)

wherein, ring A is an aromatic or heterocyclic ring condensed with the adjacent rings and represented by formula (1b), ring B is a heterocyclic ring condensed with the adjacent rings and represented by formula (1c), X is carbon or nitrogen, R$_{43}$ is hydrogen, a non-condensed substituted or unsubstituted aromatic hydrocarbon group, a non-condensed substituted or unsubstituted aromatic heterocyclic group, or a ring condensed with the X-containing ring, R$_{44}$ is a non-condensed substituted or unsubstituted aromatic hydrocarbon group or a non-condensed substituted or unsubstituted aromatic heterocyclic group, and each of R$_{41}$ and R$_{42}$ is hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, a substituted or unsubstituted aromatic hydrocarbon group, or a substituted or unsubstituted aromatic heterocyclic group.

12. A compound for use in an organic electroluminescent device as described in claim 1, wherein the compound is selected from the group consisting of:

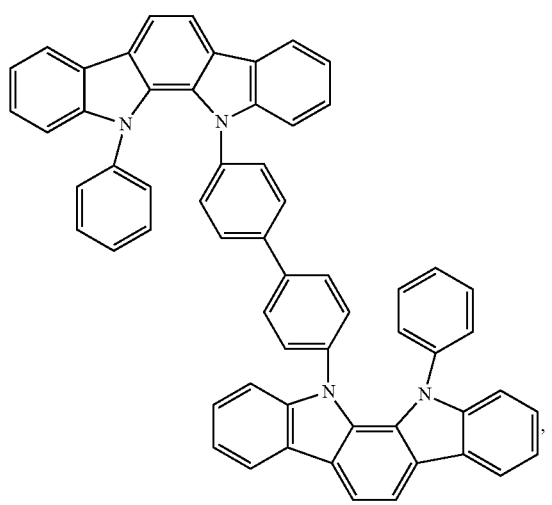

9

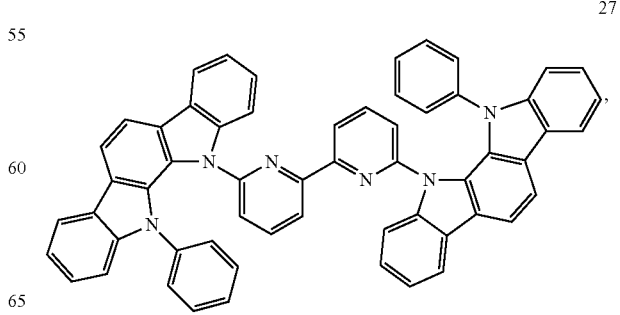

27

-continued
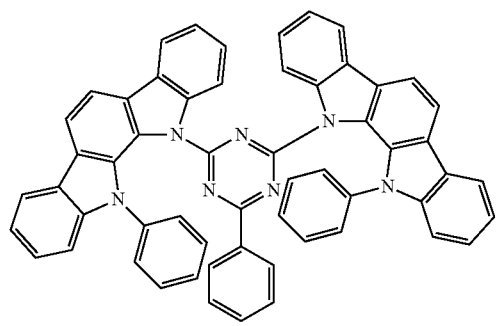
and
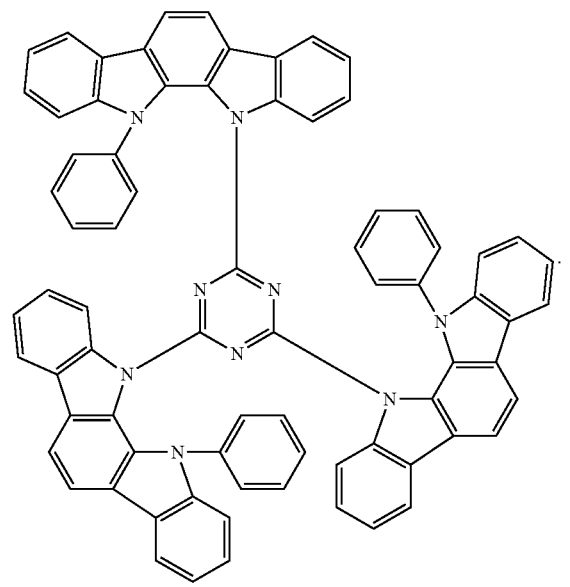
* * * * *